US009987347B2

(12) United States Patent
Weiner et al.

(10) Patent No.: US 9,987,347 B2
(45) Date of Patent: Jun. 5, 2018

(54) VACCINES AGAINST MULTIPLE SUBTYPES OF DENGUE VIRUS

(71) Applicants: INOVIO PHARMACEUTICALS, INC., Plymouth Meeting, PA (US); David B. Weiner, Merion, PA (US); Jian Yan, Wallingford, PA (US); Niranjan Sardesai, Blue Bell, PA (US)

(72) Inventors: David B. Weiner, Merion, PA (US); Jian Yan, Wallingford, PA (US); Niranjan Sardesai, Blue Bell, PA (US)

(73) Assignees: THE TRUSTEES OF THE UNIVERSITY OF PENNSYLVANIA, Philadelphia, PA (US); INOVIO PHARMACEUTICALS, INC., Plymouth Meeting, PA (US)

( * ) Notice: Subject to any disclaimer, the term of this patent is extended or adjusted under 35 U.S.C. 154(b) by 0 days. days.

(21) Appl. No.: 14/775,069

(22) PCT Filed: Mar. 14, 2014

(86) PCT No.: PCT/US2014/029341
§ 371 (c)(1),
(2) Date: Sep. 11, 2015

(87) PCT Pub. No.: WO2014/144786
PCT Pub. Date: Sep. 18, 2014

(65) Prior Publication Data
US 2016/0022802 A1 Jan. 28, 2016

Related U.S. Application Data

(60) Provisional application No. 61/801,792, filed on Mar. 15, 2013.

(51) Int. Cl.
*C07H 21/04* (2006.01)
*A61K 31/70* (2006.01)
*A61K 39/12* (2006.01)
*A61K 31/7088* (2006.01)
*A61N 1/04* (2006.01)
*A61N 1/32* (2006.01)
*C07K 14/005* (2006.01)
*C12N 7/00* (2006.01)
*A01K 67/00* (2006.01)
*A61K 39/00* (2006.01)

(52) U.S. Cl.
CPC .......... *A61K 39/12* (2013.01); *A61K 31/7088* (2013.01); *A61N 1/0412* (2013.01); *A61N 1/327* (2013.01); *C07K 14/005* (2013.01); *C12N 7/00* (2013.01); *A61K 2039/53* (2013.01); *A61K 2039/54* (2013.01); *A61K 2039/55527* (2013.01); *A61K 2039/55538* (2013.01); *A61K 2039/575* (2013.01); *A61N 1/0476* (2013.01); *C12N 2770/24122* (2013.01); *C12N 2770/24134* (2013.01); *C12N 2770/24141* (2013.01)

(58) Field of Classification Search
CPC ................ A61K 39/12; A61K 31/7088; A61K 2039/53; A61K 2039/575; A61K 2039/5538; A61N 1/0412; A61N 1/327; C12N 2770/24122; C12N 2770/24134; C07K 14/005
See application file for complete search history.

(56) References Cited

U.S. PATENT DOCUMENTS

2010/0291144 A1  11/2010  Ramanathan et al.
2012/0039937 A1  2/2012  Simmons et al.

FOREIGN PATENT DOCUMENTS

WO  2009073330 A2  6/2009
WO  WO 2009/07330  *  6/2009
WO  2012/045063 A2  4/2012

OTHER PUBLICATIONS

Schmitz et al., "Next generation dengue vaccines: A review of candidates in preclinical development", Vaccine, 29:7276-7284, (Jul. 21, 2011).
Azevedo et al., "DNA Vaccines against Dengue Virus Type 2 Based on Truncate Envelope Protein or its Domain III", Plos One, 6(7):1-8, (Jul. 11, 2011).
Apt et al., "Tetravalent neutralizing antibody response against four dengue serotypes by a single chimeric denue envelope antigen", Vaccine, 24(3):335-344, (Jan. 16, 2006).
Raviprakash et al., "A chimeric tetravalent dengue DNA vaccine elicits neutralizing antibody to allfour virus serotypes in rhesus macaques", Virology, 353(1):166-173 (Sep. 15, 2006).
Ramanathan et al., "Development of a novel DNA SynCon(TM) tetravalent dengue vaccine that elicits immune responses against four serotypes", Vaccine, 27(46):6444-6453, (Oct. 30, 2009).
Ramanathan et al., "Coimmunization with an optimized IL15 plasmid adjuvant enhances humoral immunity via stimulating B cells induced by genetically engineered DNA vaccines expressing consensus JEV and WNV E DIII",Vaccine, 27(32):4370-4380, (Jul. 9, 2009).
Laddy et al., "Heterosubtypic protection against pathogenic human and avian influenza viruses via in vivo electroporation of synthetic consensus DNA antigens", Plos One, 3(6):1-8, (Jun. 1, 2008).
Laddy et al., "Immunogenicity of novel consensus-based DNA vaccines against avian influenza", Vaccine, 25(16):2984-2989, (Mar. 29, 2007).

(Continued)

*Primary Examiner* — Quang Nguyen
(74) *Attorney, Agent, or Firm* — Riverside Law LLP

(57) ABSTRACT

An aspect of the present invention is related to nucleic acid constructs capable of expressing a polypeptide, such as a consensus dengue prME that elicits an immune response in a mammal against more than one subtype of dengue virus, and methods of use thereof. Additionally, there are DNA plasmid vaccines capable of generating in a mammal an immune response against a plurality of dengue virus subtypes, comprising a DNA plasmid and a pharmaceutically acceptable excipient, and methods of use thereof. The DNA plasmid is capable of expressing a consensus dengue antigen in a cell of the mammal in a quantity effective to elicit an immune response in the mammal that is cross reactive against all 4 dengue subtypes.

28 Claims, 17 Drawing Sheets

(56) References Cited

OTHER PUBLICATIONS

Sardesai et al., "Electroporation delivery of DNA vaccines: prospects for success", Current Opinion in Immunology, 23(3):421-429 (2011).
Konishi et al., "Dengue tetravalent DNA vaccine inducing neutralizing antibody and anamnestic responses to four serotypes in mice", Vaccine 24, pp. 2200-2207 (2006).
Wang et al., "Efficient Assembly and Secretion of Recombinant Subviral Particles of the Four Dengue Serotypes Using Native prM and E Proteins," PLoS ONE, 4(12):e8325.
Lima et al., "A DNA vaccine candidate encoding the structural prM/E proteins elicits a very strong immune response and protects mice against dengue-4 virus infection," Vaccine, 2011, 29:831-838.
Lu et al., "Preliminary evaluation of DNA vaccine candidates encoding dengue-2 prM/E and NS1: Their immunity and protective efficacy in mice," Molecular Immunology, 2013, 54:109-114.

\* cited by examiner

Comparison of binding antibodies against D1-DIII protein in mice immunized with DU or D1prME construct Comparison of binding antibodies against D2-DIII protein in mice immunized with DU or D2prME construct Comparison of binding antibodies against D3-DIII protein in mice immunized with DU or D3prME construct Comparison of binding antibodies against D4-DIII protein in mice immunized with DU or D4prME construct Vaccination with Dengue prME constructs induced anti prM/E-specific antibodies in mice.

Binding antibodies against all four DIII proteins in guinea pigs immunized with DU-DIII construct

FIGURE 9

Binding antibodies against all four DIII proteins in guinea pigs immunized with Den1-4 prME constructs Binding antibodies against all four DIII proteins in guinea pigs immunized with Den1 prME construct Binding antibodies against all four DIII proteins in guinea pigs immunized with Den2 prME construct

FIGURE 12

Binding antibodies against all four DIII proteins in guinea pigs immunized with Den3 prME construct

Neutralizing Antibodies against Dengue 3 virus

FIGURE 17

Neutralizing Antibodies against Dengue 4 virus

SEQUENCE LISTING

```
<160> NUMBER OF SEQ ID NOS: 10

<210> SEQ ID NO 1
<211> LENGTH: 2100
<212> TYPE: DNA
<213> ORGANISM: Artificial Sequence
<220> FEATURE:
<223> OTHER INFORMATION: Den1-prME DNA sequence

<400> SEQUENCE: 1
atggactgga cctggattct gtttctggtc gccgccgcaa ctagagtgca ttcaaatagg      60
aggaagagga gcgtcacaat gctgctgatg ctgatgccca ccgccctggc tttccacctg     120
accacacggg gcggggagcc tcatatgatc gtgtccaagc aggaaagagg gaaatccctg     180
ctgtttaaga cttctgccgg agtgaacatg tgcaccctga ttgctatgga cctgggcgag     240
ctgtgcgaag ataccatgac atacaagtgt ccaaggatca cagaggccga acccgacgat     300
gtggactgct ggtgtaatgc tactgatacc tgggtgacct atgggacatg ttcacagacc     360
ggagagcacc ggagagacaa gaggagcgtg gcactggccc ctcacgtcgg actgggactg     420
gagacacgca ctgaaacctg gatgagctcc gagggggcct ggaaacagat tcagagagtg     480
gaaacctggg ctctgaggca ccctggattc acagtgatcg cactgtttct ggctcatgca     540
attggaactt ctatcaccca gaagggcatc attttcattc tgctgatgct ggtgacccca     600
agtatggcaa tgcgatgcgt gggaatcgga aaccgagact ttgtcgaggg cctgtccggg     660
gctacatggg tggatgtggt cctggaacac ggctcttgtg tcactaccat ggcaaaggac     720
aaaccaaccc tggatatcga gctgctgaag acagaagtga ctaaccccgc agtcctgcga     780
aaactgtgca ttgaggccaa gatcagtaat acaactaccg attcacgctg tcccactcag     840
ggcgaagcta ccctggtgga ggaacaggac gcaaacttcg tgtgcaggcg cacctttgtc     900
gatcgcggat ggggcaatgg gtgtggactg ttcggcaagg ggtccctgat cacatgcgcc     960
```

-continued

```
aagtttaaat gtgtgactaa gctggagggc aaaattgtcc agtacgaaaa cctgaaatat    1020
tcagtcatcg tgaccgtcca cacaggcgac cagcatcaag tggggaatga gtctaccgaa    1080
cacgggacaa ctgcaacaat tactcctcag gccccaacaa gcgagatcca gctgactgac    1140
tacggagccc tgacccggaa ttgctcccct cggaccggac tggatttcaa cgagatggtg    1200
ctgctgacaa tgaaggaaaa aagttggctg gtgcataagc agtggtttct ggacctgcca    1260
ctgccctgga catctggcgc ctcaacaagc aggagactt ggaatagaca ggatctgctg     1320
gtgactttca agaccgccca cgctaagaaa caggaggtgg tcgtgctggg cagccaggaa    1380
ggagctatgc atacagcact gactggcgcc accgagattc agaccagcgg gaccacaact    1440
atcttcgccg gacacctgaa gtgccggctg aagatggaca aactgacact gaaaggaatg    1500
agctacgtga tgtgtactgg ctcctttaag ctggagaaag aagtggctga cccagcat    1560 ggcacagtgc tggtccaggt gaaatatgaa gggaccgacg cccctgtaa gatccctttc     1620 agcacccagg atgagaaagg agtgacacag aacggcaggc tgattacagc aaatcctatc   1680
gtgactgata aggaaaaacc agtcaacatt gaggccgaac cccttttgg cgagagttac     1740 atcgtcgtgg gagctggcga aaaggcactg aaactgtcat ggttcaagaa agggtctagt   1800
attggaaaga tgtttgaggc aaccgccaga ggcgcccgac gaatggctat tctgggcgac   1860
actgcttggg atttcgggtc tatcggaggc gtctttacca gtgtgggcaa gctggtccac   1920
cagatcttcg gcacagccta tggggtgctg ttttcagggg tcagctggac tatgaaaatc   1980
gggattggaa tcctgctgac ttggctggga ctgaattcca gatctaccag tctgagcatg   2040
acttgtattg ccgtcggact ggtgacactg tatctgggcg tgatggtgca ggcctgataa   2100
```

<210> SEQ ID NO 2
<211> LENGTH: 698
<212> TYPE: PRT
<213> ORGANISM: Artificial Sequence
<220> FEATURE:
<223> OTHER INFORMATION: Den1-prME protein sequence

<400> SEQUENCE: 2

```
Met Asp Trp Thr Trp Ile Leu Phe Leu Val Ala Ala Thr Arg Val
1               5                   10                  15

His Ser Asn Arg Arg Lys Arg Ser Val Thr Met Leu Leu Met Leu Met
            20                  25                  30

Pro Thr Ala Leu Ala Phe His Leu Thr Thr Arg Gly Gly Glu Pro His
        35                  40                  45

Met Ile Val Ser Lys Gln Glu Arg Gly Lys Ser Leu Leu Phe Lys Thr
    50                  55                  60

Ser Ala Gly Val Asn Met Cys Thr Leu Ile Ala Met Asp Leu Gly Glu
65                  70                  75                  80

Leu Cys Glu Asp Thr Met Thr Tyr Lys Cys Pro Arg Ile Thr Glu Ala
                85                  90                  95

Glu Pro Asp Asp Val Asp Cys Trp Cys Asn Ala Thr Asp Thr Trp Val
            100                 105                 110

Thr Tyr Gly Thr Cys Ser Gln Thr Gly Glu His Arg Arg Asp Lys Arg
        115                 120                 125

Ser Val Ala Leu Ala Pro His Val Gly Leu Gly Leu Glu Thr Arg Thr
    130                 135                 140

Glu Thr Trp Met Ser Ser Glu Gly Ala Trp Lys Gln Ile Gln Arg Val
145                 150                 155                 160
```

-continued

```
Glu Thr Trp Ala Leu Arg His Pro Gly Phe Thr Val Ile Ala Leu Phe
            165                 170                 175
Leu Ala His Ala Ile Gly Thr Ser Ile Thr Gln Lys Gly Ile Ile Phe
        180                 185                 190
Ile Leu Leu Met Leu Val Thr Pro Ser Met Ala Met Arg Cys Val Gly
            195                 200                 205
Ile Gly Asn Arg Asp Phe Val Glu Gly Leu Ser Gly Ala Thr Trp Val
        210                 215                 220
Asp Val Val Leu Glu His Gly Ser Cys Val Thr Met Ala Lys Asp
225                 230                 235                 240
Lys Pro Thr Leu Asp Ile Glu Leu Leu Lys Thr Glu Val Thr Asn Pro
            245                 250                 255
Ala Val Leu Arg Lys Leu Cys Ile Glu Ala Lys Ile Ser Asn Thr Thr
        260                 265                 270
Thr Asp Ser Arg Cys Pro Thr Gln Gly Glu Ala Thr Leu Val Glu Glu
        275                 280                 285
Gln Asp Ala Asn Phe Val Cys Arg Arg Thr Phe Val Asp Arg Gly Trp
    290                 295                 300
Gly Asn Gly Cys Gly Leu Phe Gly Lys Gly Ser Leu Ile Thr Cys Ala
305                 310                 315                 320
Lys Phe Lys Cys Val Thr Lys Leu Glu Gly Lys Ile Val Gln Tyr Glu
            325                 330                 335
Asn Leu Lys Tyr Ser Val Ile Val Thr Val His Thr Gly Asp Gln His
            340                 345                 350
Gln Val Gly Asn Glu Ser Thr Glu His Gly Thr Thr Ala Thr Ile Thr
        355                 360                 365
Pro Gln Ala Pro Thr Ser Glu Ile Gln Leu Thr Asp Tyr Gly Ala Leu
    370                 375                 380
Thr Leu Asp Cys Ser Pro Arg Thr Gly Leu Asp Phe Asn Glu Met Val
385                 390                 395                 400
Leu Leu Thr Met Lys Glu Lys Ser Trp Leu Val His Lys Gln Trp Phe
            405                 410                 415
Leu Asp Leu Pro Leu Pro Trp Thr Ser Gly Ala Ser Thr Ser Gln Glu
        420                 425                 430
Thr Trp Asn Arg Gln Asp Leu Leu Val Thr Phe Lys Thr Ala His Ala
        435                 440                 445
Lys Lys Gln Glu Val Val Val Leu Gly Ser Gln Glu Gly Ala Met His
    450                 455                 460
Thr Ala Leu Thr Gly Ala Thr Glu Ile Gln Thr Ser Gly Thr Thr Thr
465                 470                 475                 480
Ile Phe Ala Gly His Leu Lys Cys Arg Leu Lys Met Asp Lys Leu Thr
            485                 490                 495
Leu Lys Gly Met Ser Tyr Val Met Cys Thr Gly Ser Phe Lys Leu Glu
        500                 505                 510
Lys Glu Val Ala Glu Thr Gln His Gly Thr Val Leu Val Gln Val Lys
    515                 520                 525
Tyr Glu Gly Thr Asp Ala Pro Cys Lys Ile Pro Phe Ser Thr Gln Asp
    530                 535                 540
Glu Lys Gly Val Thr Gln Asn Gly Arg Leu Ile Thr Ala Asn Pro Ile
545                 550                 555                 560
Val Thr Asp Lys Glu Lys Pro Val Asn Ile Glu Ala Glu Pro Pro Phe
            565                 570                 575
Gly Glu Ser Tyr Ile Val Val Gly Ala Gly Glu Lys Ala Leu Lys Leu
```

```
                580              585              590
Ser Trp Phe Lys Lys Gly Ser Ser Ile Gly Lys Met Phe Glu Ala Thr
                    595              600              605
Ala Arg Gly Ala Arg Arg Met Ala Ile Leu Gly Asp Thr Ala Trp Asp
            610              615              620
Phe Gly Ser Ile Gly Gly Val Phe Thr Ser Val Gly Lys Leu Val His
625              630              635              640
Gln Ile Phe Gly Thr Ala Tyr Gly Val Leu Phe Ser Gly Val Ser Trp
                645              650              655
Thr Met Lys Ile Gly Ile Gly Ile Leu Leu Thr Trp Leu Gly Leu Asn
            660              665              670
Ser Arg Ser Thr Ser Leu Ser Met Thr Cys Ile Ala Val Gly Leu Val
        675              680              685
Thr Leu Tyr Leu Gly Val Met Val Gln Ala
        690              695

<210> SEQ ID NO 3
<211> LENGTH: 2100
<212> TYPE: DNA
<213> ORGANISM: Artificial Sequence
<220> FEATURE:
<223> OTHER INFORMATION: Den2-prME DNA sequence

<400> SEQUENCE: 3
atggactgga catggattct gttcctggtc gccgctgcta cacgggtgca ttcaaataga      60
cggagacgga gtgccgggat gattatcatg ctgattccaa ccgtgatggc tttccacctg     120
accacaagga acggcgagcc ccatatgatc gtgggacgcc aggaaaaggg caaatccctg     180
ctgtttaaaa ctgaggacgg agtgaatatg tgcacccctg aggcaattga cctgggcgag     240
ctgtgcgaag atactatcac ctacaagtgt ccactgctga ggcagaacga gcccgaagac     300
atcgattgct ggtgtaatag tacatcaact tgggtgactt atggcacctg tactaccaca     360
ggggagcacc ggagagaaaa gagatctgtc gctctggtgc ccatgtcgg catggggctg      420
gagaccagga cagaaacttg gatgagctcc gagggcgcat ggaagcacgt gcagcgcatt     480
gaaacatgga ttctgcgaca tcctgggttc actattatgg ccgctatcct ggcctacacc     540
attggaacta cccacttcca gcgcgctctg atttttatcc tgctgacagc tgtggcacca     600
tccatgacta tgcggtgcat tggcatctct aacagagact cgtggagggg gtcagcggc      660
gggtcctggg tggatatcgt cctggaacat ggcagctgtg tgacaactat ggcaaagaac     720
aagcctaccc tggattttga gctgatcaag accgaagcca agcagccagc tacactgcgc     780
aaatattgca tcgaggccaa gctgaccaac accacaactg agagtcgatg tcccacacag     840
ggggaacctt cactgaatga ggaacaggac aaacgatttg tgtgcaagca cagcatggtc     900
gatcggggat ggggcaacgg tgtggactg ttcggaaaag gaggcattgt gacatgcgcc      960
atgtttactt gtaagaaaaa catggaggc aagatcgtgc agcccgagaa tctggaatac     1020
accattgtca tcacacctca ctccggagag aacatgccg tgggcaatga cactgggaag     1080
cacggaaaag agattaaggt caccccctcag tctagtatca ccgaggctga actgacaggc     1140
tatgggaccg tgacaatgga atgctctcct cggacaggcc tggatttcaa cgagatggtg     1200
ctgctgcaga tggaaaataa ggcatggctg gtccatagac agtggtttct ggacctgcca     1260
ctgccatggc tgccaggagc agatacccag ggatctaact ggattcagaa agagacactg     1320
gtgactttca agaatccca cgccaagaaa caggacgtgg tcgtgctggg cagtcaggag     1380
```

```
ggagcaatgc ataccgccct gacaggcgct actgaaatcc agatgtcaag cgggaacctg    1440
ctgttcacag gacacctgaa atgcaggctg cgcatggata aactgcagct gaagggggatg   1500 agctactcca tgtgtaccgg aaagtttaaa gtcgtgaagg agatcgccga aactcagcac   1560
ggcaccattg tgatccgggt ccagtatgag ggagacggca gcccttgtaa aattccattc    1620
gagatcatgg atctggaaaa agacatgtg ctggggaggc tgattactgt gaaccctatc    1680
gtcaccgaga aggacagccc agtgaatatc gaggctgaac ccccttttgg agattcctac   1740
atcattatcg gagtggagcc tggccagctg aaactgaact ggttcaagaa agggtcctct   1800
attggacaga tgtttgaaac cacaatgcga ggcgcaaagc ggatggccat cctgggcgac   1860
acagcctggg atttcgggtc actgggcggc gtgttcacca gcattggcaa agctctgcac   1920
caggtcttcg gcgcaatcta tggggcagcc ttttctgggg tgagttggac catgaagatt   1980
ctgatcggag tcattatcac atggatcggc atgaattcta gaagtacttc actgtccgtg   2040
agcctggtcc tggtcggcgt ggtgacactg tatctgggcg tgatggtgca ggcctgataa   2100
```

```
<210> SEQ ID NO 4
<211> LENGTH: 698
<212> TYPE: PRT
<213> ORGANISM: Artificial Sequence
<220> FEATURE:
<223> OTHER INFORMATION: Den2-prME protein sequence

<400> SEQUENCE: 4

Met Asp Trp Thr Trp Ile Leu Phe Leu Val Ala Ala Thr Arg Val
1               5                   10                  15

His Ser Asn Arg Arg Arg Ser Ala Gly Met Ile Ile Met Leu Ile
            20                  25                  30

Pro Thr Val Met Ala Phe His Leu Thr Thr Arg Asn Gly Glu Pro His
        35                  40                  45

Met Ile Val Gly Arg Gln Glu Lys Gly Lys Ser Leu Leu Phe Lys Thr
    50                  55                  60

Glu Asp Gly Val Asn Met Cys Thr Leu Met Ala Ile Asp Leu Gly Glu
65                  70                  75                  80

Leu Cys Glu Asp Thr Ile Thr Tyr Lys Cys Pro Leu Leu Arg Gln Asn
                85                  90                  95

Glu Pro Glu Asp Ile Asp Cys Trp Cys Asn Ser Thr Ser Thr Trp Val
            100                 105                 110

Thr Tyr Gly Thr Cys Thr Thr Thr Gly Glu His Arg Arg Glu Lys Arg
        115                 120                 125

Ser Val Ala Leu Val Pro His Val Gly Met Gly Leu Glu Thr Arg Thr
    130                 135                 140

Glu Thr Trp Met Ser Ser Glu Gly Ala Trp Lys His Val Gln Arg Ile
145                 150                 155                 160

Glu Thr Trp Ile Leu Arg His Pro Gly Phe Thr Ile Met Ala Ala Ile
                165                 170                 175

Leu Ala Tyr Thr Ile Gly Thr Thr His Phe Gln Arg Ala Leu Ile Phe
            180                 185                 190

Ile Leu Leu Thr Ala Val Ala Pro Ser Met Thr Met Arg Cys Ile Gly
        195                 200                 205

Ile Ser Asn Arg Asp Phe Val Glu Gly Val Ser Gly Gly Ser Trp Val
    210                 215                 220

Asp Ile Val Leu Glu His Gly Ser Cys Val Thr Thr Met Ala Lys Asn
225                 230                 235                 240
```

```
Lys Pro Thr Leu Asp Phe Glu Leu Ile Lys Thr Glu Ala Lys Gln Pro
            245                 250                 255

Ala Thr Leu Arg Lys Tyr Cys Ile Glu Ala Lys Leu Thr Asn Thr Thr
        260                 265                 270

Thr Glu Ser Arg Cys Pro Thr Gln Gly Glu Pro Ser Leu Asn Glu Glu
        275                 280                 285

Gln Asp Lys Arg Phe Val Cys Lys His Ser Met Val Asp Arg Gly Trp
        290                 295                 300

Gly Asn Gly Cys Gly Leu Phe Gly Lys Gly Ile Val Thr Cys Ala
305                 310                 315                 320

Met Phe Thr Cys Lys Lys Asn Met Glu Gly Lys Ile Val Gln Pro Glu
                325                 330                 335

Asn Leu Glu Tyr Thr Ile Val Ile Thr Pro His Ser Gly Glu Glu His
            340                 345                 350

Ala Val Gly Asn Asp Thr Gly Lys His Gly Lys Glu Ile Lys Val Thr
        355                 360                 365

Pro Gln Ser Ser Ile Thr Glu Ala Glu Leu Thr Gly Tyr Gly Thr Val
    370                 375                 380

Thr Met Glu Cys Ser Pro Arg Thr Gly Leu Asp Phe Asn Glu Met Val
385                 390                 395                 400

Leu Leu Gln Met Glu Asn Lys Ala Trp Leu Val His Arg Gln Trp Phe
            405                 410                 415

Leu Asp Leu Pro Leu Pro Trp Leu Pro Gly Ala Asp Thr Gln Gly Ser
        420                 425                 430

Asn Trp Ile Gln Lys Glu Thr Leu Val Thr Phe Lys Asn Pro His Ala
        435                 440                 445

Lys Lys Gln Asp Val Val Val Leu Gly Ser Gln Glu Gly Ala Met His
    450                 455                 460

Thr Ala Leu Thr Gly Ala Thr Glu Ile Gln Met Ser Ser Gly Asn Leu
465                 470                 475                 480

Leu Phe Thr Gly His Leu Lys Cys Arg Leu Arg Met Asp Lys Leu Gln
            485                 490                 495

Leu Lys Gly Met Ser Tyr Ser Met Cys Thr Gly Lys Phe Lys Val Val
        500                 505                 510

Lys Glu Ile Ala Glu Thr Gln His Gly Thr Ile Val Ile Arg Val Gln
    515                 520                 525

Tyr Glu Gly Asp Gly Ser Pro Cys Lys Ile Pro Phe Glu Ile Met Asp
        530                 535                 540

Leu Glu Lys Arg His Val Leu Gly Arg Leu Ile Thr Val Asn Pro Ile
545                 550                 555                 560

Val Thr Glu Lys Asp Ser Pro Val Asn Ile Glu Ala Glu Pro Pro Phe
            565                 570                 575

Gly Asp Ser Tyr Ile Ile Ile Gly Val Glu Pro Gly Gln Leu Lys Leu
        580                 585                 590

Asn Trp Phe Lys Lys Gly Ser Ser Ile Gly Gln Met Phe Glu Thr Thr
        595                 600                 605

Met Arg Gly Ala Lys Arg Met Ala Ile Leu Gly Asp Thr Ala Trp Asp
    610                 615                 620

Phe Gly Ser Leu Gly Gly Val Phe Thr Ser Ile Gly Lys Ala Leu His
625                 630                 635                 640

Gln Val Phe Gly Ala Ile Tyr Gly Ala Ala Phe Ser Gly Val Ser Trp
            645                 650                 655

Thr Met Lys Ile Leu Ile Gly Val Ile Ile Thr Trp Ile Gly Met Asn
```

Ser Arg Ser Thr Ser Leu Ser Val Ser Leu Val Leu Val Gly Val Val
660               665               670
        675               680               685
Thr Leu Tyr Leu Gly Val Met Val Gln Ala
690               695

<210> SEQ ID NO 5
<211> LENGTH: 2094
<212> TYPE: DNA
<213> ORGANISM: Artificial Sequence
<220> FEATURE:
<223> OTHER INFORMATION: Den3-prME DNA sequence

<400> SEQUENCE: 5

| | |
|---|---|
| atggactgga cctggattct gttcctggtc gccgccgcaa cccgcgtgca ttcaaacaaa | 60 |
| agaaagaaaa cttcactgtg cctgatgatg atgctgccag ccactctggc tttccacctg | 120 |
| accagccgag acggagaacc acggatgatc gtgggcaaga cgagaggggg gaaaagtctg | 180 |
| ctgtttaaga ccgcttcagg cattaatatg tgcacactga tcgcaatgga tctgggggag | 240 |
| atgtgcgacg ataccgtcac atacaagtgt ccccatatta ccgaggtgga acctgaggac | 300 |
| atcgattgct ggtgtaacct gactagtacc tgggtgactt atgggacctg taatcaggcc | 360 |
| ggagagcacc ggagagacaa gagatcagtc gccctggctc ctcatgtggg catggggctg | 420 |
| gatacaagaa ctcagacctg gatgagcgca gagggagcat ggcgacaggt cgaaaaagtg | 480 |
| gagacttggg ccctgcgaca ccctggattc accattctgg ccctgttcct ggctcattac | 540 |
| atcggcacat cactgactca gaaggtggtc atcttcattc tgctgatgct ggtgacacca | 600 |
| agcatgacta tgagatgcgt cggagtgggc aacagggact tgtcgaaagg ctgtccgga | 660 |
| gccacctggg tggatgtggt cctggagcac ggcggatgtg tgaccacaat ggctaagaac | 720 |
| aagccaaccc tggacattga actgcagaag accgaggcaa cacagctggc cacactgagg | 780 |
| aaactgtgca tcgaagggaa gattactaac atcactaccg attcccgctg tccaacccag | 840 |
| ggagaggctg tgctgcccga ggaacaggac cagaactacg tctgcaagca tacatatgtg | 900 |
| gatagagggt ggggaaatgg ctgtgggctg ttcggaaaag ctctctctgg tgacctgcgcc | 960 |
| aagtttcagt gtctggaacc catcgaggga aaagtggtcc agtacgagaa cctgaagtat | 1020 |
| acagtcatca ttactgtgca caccggcgac cagcatcagg tcggaaatga acccagggc | 1080 |
| gtgacagccg agattactcc ccaggcctcc accgtggaag ctatcctgcc tgagtatggc | 1140 |
| acactggggc tggaatgctc tccccgaact ggcctggact caacgagat gatcctgctg | 1200 |
| acaatgaaga caaggcttg gatggtgcac cgccagtggt tctttgatct gccactgccc | 1260 |
| tggacttccg gcgcaacaac tgaaacacct acttggaacc ggaaagagct gctggtgacc | 1320 |
| tttaagaatg cacacgccaa gaaacaggaa gtggtcgtgc tgggatctca ggagggcgct | 1380 |
| atgcatacag cactgactgg cgccaccgaa attcagaact caggaggcac cagcatcttc | 1440 |
| gctgggcacc tgaaatgcag actgaagatg gacaaactgg agctgaaggg aatgtcttac | 1500 |
| gccatgtgta ccaatacatt tgtcctgaag aaagaagtga gtgagaccca gcacgggaca | 1560 |
| atcctgatta aggtgaata aaggagag acgcccctt gtaaaatccc attcagtacc | 1620 |
| gaggatgggc agggaaaggc acataacggg aggctgatta cagccaatcc tgtcgtgact | 1680 |
| aagaaagagg aaccagtgaa catcgaagca gagccccctt ttggcgaaag caatatcgtg | 1740 |
| attggcatcg gggataaggc cctgaaaatt aactggtaca gaaagggag ctccatcgga | 1800 |
| aaaatgttcg aggctacagc acgcggcgct aggcgaatgg caattctggg cgacactgcc | 1860 |

-continued

```
tgggattttg ggagcgtcgg gggagtgctg aattccctgg gaaagatggt gcaccagatc    1920
ttcggcagcg cttataccgc actgttttct ggcgtcagtt ggattatgaa aattggaatc    1980
ggcgtgctgc tgacctggat cgggctgaac tccaagaata catctatgtc cttttcatgt    2040
attgctattg gaattattac tctgtatctg ggagccgtgg tgcaggcctg ataa          2094
```

<210> SEQ ID NO 6
<211> LENGTH: 696
<212> TYPE: PRT
<213> ORGANISM: Artificial Sequence
<220> FEATURE:
<223> OTHER INFORMATION: Den3-prME protein sequence

<400> SEQUENCE: 6

```
Met Asp Trp Thr Trp Ile Leu Phe Leu Val Ala Ala Thr Arg Val
1               5                   10                  15

His Ser Asn Lys Arg Lys Lys Thr Ser Leu Cys Leu Met Met Met Leu
                20                  25                  30

Pro Ala Thr Leu Ala Phe His Leu Thr Ser Arg Asp Gly Glu Pro Arg
                35                  40                  45

Met Ile Val Gly Lys Asn Glu Arg Gly Lys Ser Leu Leu Phe Lys Thr
        50                  55                  60

Ala Ser Gly Ile Asn Met Cys Thr Leu Ile Ala Met Asp Leu Gly Glu
65                  70                  75                  80

Met Cys Asp Asp Thr Val Thr Tyr Lys Cys Pro His Ile Thr Glu Val
                85                  90                  95

Glu Pro Glu Asp Ile Asp Cys Trp Cys Asn Leu Thr Ser Thr Trp Val
                100                 105                 110

Thr Tyr Gly Thr Cys Asn Gln Ala Gly Glu His Arg Arg Asp Lys Arg
            115                 120                 125

Ser Val Ala Leu Ala Pro His Val Gly Met Gly Leu Asp Thr Arg Thr
    130                 135                 140

Gln Thr Trp Met Ser Ala Glu Gly Ala Trp Arg Gln Val Glu Lys Val
145                 150                 155                 160

Glu Thr Trp Ala Leu Arg His Pro Gly Phe Thr Ile Leu Ala Leu Phe
                165                 170                 175

Leu Ala His Tyr Ile Gly Thr Ser Leu Thr Gln Lys Val Val Ile Phe
                180                 185                 190

Ile Leu Leu Met Leu Val Thr Pro Ser Met Thr Met Arg Cys Val Gly
            195                 200                 205

Val Gly Asn Arg Asp Phe Val Glu Gly Leu Ser Gly Ala Thr Trp Val
    210                 215                 220

Asp Val Val Leu Glu His Gly Gly Cys Val Thr Thr Met Ala Lys Asn
225                 230                 235                 240

Lys Pro Thr Leu Asp Ile Glu Leu Gln Lys Thr Glu Ala Thr Gln Leu
                245                 250                 255

Ala Thr Leu Arg Lys Leu Cys Ile Glu Gly Lys Ile Thr Asn Ile Thr
                260                 265                 270

Thr Asp Ser Arg Cys Pro Thr Gln Gly Glu Ala Val Leu Pro Glu Glu
            275                 280                 285

Gln Asp Gln Asn Tyr Val Cys Lys His Thr Tyr Val Asp Arg Gly Trp
    290                 295                 300

Gly Asn Gly Cys Gly Leu Phe Gly Lys Gly Ser Leu Val Thr Cys Ala
305                 310                 315                 320
```

```
Lys Phe Gln Cys Leu Glu Pro Ile Glu Gly Lys Val Val Gln Tyr Glu
                325                 330                 335

Asn Leu Lys Tyr Thr Val Ile Ile Thr Val His Thr Gly Asp Gln His
            340                 345                 350

Gln Val Gly Asn Glu Thr Gln Gly Val Thr Ala Glu Ile Thr Pro Gln
        355                 360                 365

Ala Ser Thr Val Glu Ala Ile Leu Pro Glu Tyr Gly Thr Leu Gly Leu
    370                 375                 380

Glu Cys Ser Pro Arg Thr Gly Leu Asp Phe Asn Glu Met Ile Leu Leu
385                 390                 395                 400

Thr Met Lys Asn Lys Ala Trp Met Val His Arg Gln Trp Phe Phe Asp
                405                 410                 415

Leu Pro Leu Pro Trp Thr Ser Gly Ala Thr Thr Glu Thr Pro Thr Trp
            420                 425                 430

Asn Arg Lys Glu Leu Leu Val Thr Phe Lys Asn Ala His Ala Lys Lys
        435                 440                 445

Gln Glu Val Val Val Leu Gly Ser Gln Glu Gly Ala Met His Thr Ala
    450                 455                 460

Leu Thr Gly Ala Thr Glu Ile Gln Asn Ser Gly Gly Thr Ser Ile Phe
465                 470                 475                 480

Ala Gly His Leu Lys Cys Arg Leu Lys Met Asp Lys Leu Glu Leu Lys
                485                 490                 495

Gly Met Ser Tyr Ala Met Cys Thr Asn Thr Phe Val Leu Lys Lys Glu
            500                 505                 510

Val Ser Glu Thr Gln His Gly Thr Ile Leu Ile Lys Val Glu Tyr Lys
        515                 520                 525

Gly Glu Asp Ala Pro Cys Lys Ile Pro Phe Ser Thr Glu Asp Gly Gln
    530                 535                 540

Gly Lys Ala His Asn Gly Arg Leu Ile Thr Ala Asn Pro Val Val Thr
545                 550                 555                 560

Lys Lys Glu Glu Pro Val Asn Ile Glu Ala Glu Pro Pro Phe Gly Glu
                565                 570                 575

Ser Asn Ile Val Ile Gly Ile Gly Asp Lys Ala Leu Lys Ile Asn Trp
            580                 585                 590

Tyr Lys Lys Gly Ser Ser Ile Gly Lys Met Phe Glu Ala Thr Ala Arg
        595                 600                 605

Gly Ala Arg Arg Met Ala Ile Leu Gly Asp Thr Ala Trp Asp Phe Gly
    610                 615                 620

Ser Val Gly Gly Val Leu Asn Ser Leu Gly Lys Met Val His Gln Ile
625                 630                 635                 640

Phe Gly Ser Ala Tyr Thr Ala Leu Phe Ser Gly Val Ser Trp Ile Met
                645                 650                 655

Lys Ile Gly Ile Gly Val Leu Leu Thr Trp Ile Gly Leu Asn Ser Lys
            660                 665                 670

Asn Thr Ser Met Ser Phe Ser Cys Ile Ala Ile Gly Ile Ile Thr Leu
        675                 680                 685

Tyr Leu Gly Ala Val Val Gln Ala
    690                 695

<210> SEQ ID NO 7
<211> LENGTH: 2100
<212> TYPE: DNA
<213> ORGANISM: Artificial Sequence
<220> FEATURE:
<223> OTHER INFORMATION: Den4-prME DNA sequence
```

<400> SEQUENCE: 7

```
atggactgga cttggattct gttcctggtc gccgccgcaa ctagggtgca ttcaaacggg      60
agaaaaaggt caactattac tctgctgtgc ctgattccca ccgtcatggc attccacctg     120
agcacaagag acggggagcc actgatgatc gtggccaaac atgaacgggg agacccctg     180
ctgtttaaaa ccacagaggg aattaacaag tgtacactga tcgccatgga cctgggcgag     240
atgtgcgaag ataccgtcac atacaagtgt cctctgctgg tgaacaccga gccagaagac     300
attgattgct ggtgtaatct gacttccacc tgggtcatgt atggaacatg cactcagtct     360
ggcgagcgga aagggaaaa acgatccgtg gctctgaccc ctcactctgg gatgggactg     420
gagacccggg cagaaacatg gatgagctcc gagggcgcct ggaagcatgc tcagagagtg     480
gaatcctgga ttctgaggaa ccctgggttc gctctgctgg caggcttcat ggcatacatg     540
attggccaga ctggcatcca gcgcaccgtc ttctttgtgc tgatgatgct ggtggcccca     600
agttatggaa tgcgctgcgt cggcgtgggg aatcgagact cgtcgagggg cgtgtcaggc     660
ggggcttggg tcgatctggt gctggaacac ggaggctgtg tgactaccat ggcacagggc     720
aagcctactc tggactttga gctgaccaaa acaactgcaa aggaagtggc cctgctgcgc     780
acctactgca ttgaggcctc catttctaac atcaccacag ctactcggtg tccaacccag     840
ggagaaccct acctgaaaga ggaacaggat cagcagtata tctgccgacg agacgtggtc     900
gatcgaggat ggggcaatgg gtgtggactg ttcggcaagg gcggcgtggt cacttgcgcc     960
aagttcagct gttcaggaaa gattaccggc aacctggtgc agatcgagaa tctggaatac    1020
acagtggtcg tgactgtcca caatggcgac acacatgcag tggggaacga tacttctaat    1080
cacggcgtga ccgccacaat cactcctaga agcccatccg tcgaggtgaa gctgcccgac    1140
tatgcgagc tgacactgga ttgcgaacct aggagtggga ttgacttcaa cgagatgatc    1200
ctgatgaaaa tgaagaaaaa gacctggctg gtgcataagc agtggtttct ggacctgcca    1260
ctgccatgga cagcaggagc tgatactagc gaggtgcact ggaattataa ggaaaggatg    1320
gtcacattca agtgccaca tgccaagcgc caggatgtca ctgtgctggg gagtcaggag    1380
ggagctatgc actcagcact ggcaggagct accgaagtgg acagcggcga tgggaaccac    1440
atgttcgccg acatctgaa atgcaaggtg cgaatggaga aactgcggat taagggcatg    1500
tcctacacta tgtgttctgg caagttcagc atcgacaagg agatggccga aacccagcac    1560
ggcactaccg tcgtgaaagt gaagtatgag ggagcaggcg cccctgtaa ggtccctatc    1620
gagattcgga tgtgaacaa ggaaaaggtc gtgggcagaa tcatttctag taccccctctg    1680
gctgagaaca ccaattctgt gacaaacatc gagctggaac cccctttcgg ggactcttac    1740
atcgtcattg gggtgggaaa tagtgccctg acactgcact ggttccggaa aggctcaagc    1800
attgggaaga tgtttgagag cacttatagg ggcgctaaac gcatggcaat cctgggagaa    1860
accgcatggg atttccggcag cgtgggcggg ctgtttacat ccctgggaaa ggctgtccat    1920
caggtgttcg gctcagtcta cacaactatg tttggaggcg tgagctggat gatcagaatt    1980
ctgatcgggt ttctggtgct gtggatcgga accaactcaa ggaatacaag catggctatg    2040
acttgtattg ccgtgggcgg aattacactg tttctgggat tcactgtgca ggcttgataa    2100
```

<210> SEQ ID NO 8
<211> LENGTH: 698
<212> TYPE: PRT
<213> ORGANISM: Artificial Sequence
<220> FEATURE:

<223> OTHER INFORMATION: Den4-prME Protein sequence

<400> SEQUENCE: 8

```
Met Asp Trp Thr Trp Ile Leu Phe Leu Val

-continued

```
Leu Met Lys Met Lys Lys Lys Thr Trp Leu Val His Lys Gln Trp Phe
                405                 410                 415

Leu Asp Leu Pro Leu Pro Trp Thr Ala Gly Ala Asp Thr Ser Glu Val
            420                 425                 430

His Trp Asn Tyr Lys Glu Arg Met Val Thr Phe Lys Val Pro His Ala
        435                 440                 445

Lys Arg Gln Asp Val Thr Val Leu Gly Ser Gln Glu Gly Ala Met His
    450                 455                 460

Ser Ala Leu Ala Gly Ala Thr Glu Val Asp Ser Gly Asp Gly Asn His
465                 470                 475                 480

Met Phe Ala Gly His Leu Lys Cys Lys Val Arg Met Glu Lys Leu Arg
                485                 490                 495

Ile Lys Gly Met Ser Tyr Thr Met Cys Ser Gly Lys Phe Ser Ile Asp
            500                 505                 510

Lys Glu Met Ala Glu Thr Gln His Gly Thr Thr Val Val Lys Val Lys
        515                 520                 525

Tyr Glu Gly Ala Gly Ala Pro Cys Lys Val Pro Ile Glu Ile Arg Asp
    530                 535                 540

Val Asn Lys Glu Lys Val Val Gly Arg Ile Ile Ser Ser Thr Pro Leu
545                 550                 555                 560

Ala Glu Asn Thr Asn Ser Val Thr Asn Ile Glu Leu Glu Pro Pro Phe
                565                 570                 575

Gly Asp Ser Tyr Ile Val Ile Gly Val Gly Asn Ser Ala Leu Thr Leu
            580                 585                 590

His Trp Phe Arg Lys Gly Ser Ser Ile Gly Lys Met Phe Glu Ser Thr
        595                 600                 605

Tyr Arg Gly Ala Lys Arg Met Ala Ile Leu Gly Glu Thr Ala Trp Asp
    610                 615                 620

Phe Gly Ser Val Gly Gly Leu Phe Thr Ser Leu Gly Lys Ala Val His
625                 630                 635                 640

Gln Val Phe Gly Ser Val Tyr Thr Thr Met Phe Gly Gly Val Ser Trp
                645                 650                 655

Met Ile Arg Ile Leu Ile Gly Phe Leu Val Leu Trp Ile Gly Thr Asn
            660                 665                 670

Ser Arg Asn Thr Ser Met Ala Met Thr Cys Ile Ala Val Gly Gly Ile
        675                 680                 685

Thr Leu Phe Leu Gly Phe Thr Val Gln Ala
    690                 695
```

<210> SEQ ID NO 9
<211> LENGTH: 1515
<212> TYPE: DNA
<213> ORGANISM: Artificial Sequence
<220> FEATURE:
<223> OTHER INFORMATION: Universal Dengue Antigen DNA

<400> SEQUENCE: 9

```
aagggcacca gctacgtgat gtgcaccggc agcttcaagc tggaaaaaga ggtggccgag      60
actcagcacg gcactgtgct cgtccaggtc aagtacgagg gcaccgacgc cccctgcaag     120
atccccttca gcacccaaga cgagaagggc gtgacacaga acggccggct gatcaccgcc     180
aaccccatcg tgaccgacaa agaaaagccc gtgaacatcg agaccgagcc ccccttcggc     240
gagagctaca tcgtggtggg agccggcgag aaggccctca agctgagttg gttcaaaaag     300
ggcagcagca tcggcaagat gttcgaggcc accgccaggg gcgctcgcag gatggctatt     360

-continued

```
ctccggggca ggaagcggcg gagcaagggc atgtcctaca gcatgtgtac tggcaagttc    420
aaggtcgtca agagatcgc cgaaacacaa cacgggacca tcgtgatccg ggtgcagtat    480
gagggcgacg gcagcccttg taagatccct ttcgagatca tggacctgga aaagcggcac    540
gtgctgggcc gcctgatcac agtgaatcct atcgtgacag agaaggacag ccctgtgaat    600
attgaggcag agccaccatt tggcgactcc tacatcatca tcggcgtgga gcccggccag    660
ctgaagctga attggtttaa aagggggtcc tccattgggc agatgtttga gactactatg    720
agaggcgcca agagaatggc tattctcaga ggccggaaga aaggtccaa gggcatgagt    780
tacgcaatgt gtctgaacac cttcgtgctg aagaaagaag tgagcgagac acagcatggc    840
acaatcctga ttaaggtgga gtacaagggc gaggatgccc cttgcaagat tccattctcc    900
accgaggacg gccagggcaa ggctcacaac ggcagactga ttacagccaa ccctgtggtg    960
accaagaaag aggaaccagt caatatcgaa gccgaaccac cattcggcga gtccaacatt    1020
gtgatcggca ttggcgataa agccctgaaa atcaactggt ataagaaggg ctcaagcata    1080
gggaaaatgt ttgaggcaac tgcccgcgga gcaagaagaa tggctatctt gcgtgggaga    1140
aagcgccggt caaagggcat gtcttacact atgtgctctg aaagttcag catcgacaaa    1200
gagatggctg aaacccagca tggaaccacc gtggtgaagg tgaaatatga aggcgctggg    1260
gctccctgta aggtgcccat cgagatcagg gacgtgaaca agaaaaagt ggtgggccgg    1320
atcatcagca gcaccccttt cgccgagaac accaacagcg tgaccaacat cgagctggaa    1380
ccccctttcg gcgattctta tatcgtgatt ggcgtgggcg actccgccct gaccctgcac    1440
tggttccgga agggctcctc tataggaaag atgtttgaaa gcacctaccg gggagccaaa    1500
cgcatggcca tcctg                                                     1515
```

<210> SEQ ID NO 10
<211> LENGTH: 505
<212> TYPE: PRT
<213> ORGANISM: Artificial Sequence
<220> FEATURE:
<223> OTHER INFORMATION: Universal Dengue Antigen

<400> SEQUENCE: 10

```
Lys Gly Thr Ser Tyr Val Met Cys Thr Gly Ser Phe Lys Leu Glu Lys
1               5                   10                  15

Glu Val Ala Glu Thr Gln His Gly Thr Val Leu Val Gln Val Lys Tyr
            20                  25                  30

Glu Gly Thr Asp Ala Pro Cys Lys Ile Pro Phe Ser Thr Gln Asp Glu
        35                  40                  45

Lys Gly Val Thr Gln Asn Gly Arg Leu Ile Thr Ala Asn Pro Ile Val
    50                  55                  60

Thr Asp Lys Glu Lys Pro Val Asn Ile Glu Thr Pro Pro Phe Gly
65                  70                  75                  80

Glu Ser Tyr Ile Val Val Gly Ala Gly Glu Lys Ala Leu Lys Leu Ser
                85                  90                  95

Trp Phe Lys Lys Gly Ser Ser Ile Gly Lys Met Phe Glu Ala Thr Ala
            100                 105                 110

Arg Gly Ala Arg Arg Met Ala Ile Leu Arg Gly Arg Lys Arg Arg Ser
        115                 120                 125

Lys Gly Met Ser Tyr Ser Met Cys Thr Gly Lys Phe Lys Val Val Lys
    130                 135                 140

Glu Ile Ala Glu Thr Gln His Gly Thr Ile Val Ile Arg Val Gln Tyr
145                 150                 155                 160
```

-continued

```
Glu Gly Asp Gly Ser Pro Cys Lys Ile Pro Phe Glu Ile Met Asp Leu
                165                 170                 175
Glu Lys Arg His Val Leu Gly Arg Leu Ile Thr Val Asn Pro Ile Val
            180                 185                 190
Thr Glu Lys Asp Ser Pro Val Asn Ile Glu Ala Glu Pro Pro Phe Gly
        195                 200                 205
Asp Ser Tyr Ile Ile Ile Gly Val Glu Pro Gly Gln Leu Lys Leu Asn
    210                 215                 220
Trp Phe Lys Lys Gly Ser Ser Ile Gly Gln Met Phe Glu Thr Thr Met
225                 230                 235                 240
Arg Gly Ala Lys Arg Met Ala Ile Leu Arg Gly Arg Lys Arg Arg Ser
            245                 250                 255
Lys Gly Met Ser Tyr Ala Met Cys Leu Asn Thr Phe Val Leu Lys Lys
            260                 265                 270
Glu Val Ser Glu Thr Gln His Gly Thr Ile Leu Ile Lys Val Glu Tyr
        275                 280                 285
Lys Gly Glu Asp Ala Pro Cys Lys Ile Pro Phe Ser Thr Glu Asp Gly
    290                 295                 300
Gln Gly Lys Ala His Asn Gly Arg Leu Ile Thr Ala Asn Pro Val Val
305                 310                 315                 320
Thr Lys Lys Glu Glu Pro Val Asn Ile Glu Ala Glu Pro Pro Phe Gly
            325                 330                 335
Glu Ser Asn Ile Val Ile Gly Ile Gly Asp Lys Ala Leu Lys Ile Asn
            340                 345                 350
Trp Tyr Lys Lys Gly Ser Ser Ile Gly Lys Met Phe Glu Ala Thr Ala
            355                 360                 365
Arg Gly Ala Arg Arg Met Ala Ile Leu Arg Gly Arg Lys Arg Arg Ser
    370                 375                 380
Lys Gly Met Ser Tyr Thr Met Cys Ser Gly Lys Phe Ser Ile Asp Lys
385                 390                 395                 400
Glu Met Ala Glu Thr Gln His Gly Thr Thr Val Val Lys Val Lys Tyr
            405                 410                 415
Glu Gly Ala Gly Ala Pro Cys Lys Val Pro Ile Glu Ile Arg Asp Val
            420                 425                 430
Asn Lys Glu Lys Val Val Gly Arg Ile Ile Ser Ser Thr Pro Phe Ala
            435                 440                 445
Glu Asn Thr Asn Ser Val Thr Asn Ile Glu Leu Glu Pro Pro Phe Gly
    450                 455                 460
Asp Ser Tyr Ile Val Ile Gly Val Gly Asp Ser Ala Leu Thr Leu His
465                 470                 475                 480
Trp Phe Arg Lys Gly Ser Ser Ile Gly Lys Met Phe Glu Ser Thr Tyr
            485                 490                 495
Arg Gly Ala Lys Arg Met Ala Ile Leu
            500                 505
```

VACCINES AGAINST MULTIPLE SUBTYPES OF DENGUE VIRUS

CROSS-REFERENCE TO RELATED APPLICATIONS

This application is the U.S. national stage application filed under 35 U.S.C. § 371 claiming benefit to International Patent Application No. PCT/US14/029341, filed Mar. 14, 2014, which is entitled to priority under 35 U.S.C. § 119(e) to U.S. Provisional Application No. 61/801,792, filed Mar. 15, 2013, each of which is hereby incorporated by reference in its entirety.

FIELD OF THE INVENTION

The present invention relates to improved dengue vaccines, improved methods for inducing immune responses, and for prophylactically and/or therapeutically immunizing individuals against dengue virus.

BACKGROUND

Dengue virus (DENV) is an emerging mosquito-borne pathogen that causes dengue fever (DF) and severe life threatening illness, dengue hemorrhagic fever/dengue shock syndrome (DHF/DSS). DENV is a small, enveloped, positive-stranded RNA virus that belongs to the Flavivirus genus of the Flaviviridae family. Four distinct subtypes or serotypes of dengue viruses (DV-1 to DV-4) are transmitted to humans through the bites of mosquito species *Aedes aegypti* and *Aedes albopictus*. It has been estimated that 50-100 million cases of DF and 250,000-500000 cases of DHF occur every year. Dengue constitutes a significant international public health concern, as two-fifths of the world's population live in dengue endemic regions, and an estimated 50-100 million cases of dengue infection occur annually. Furthermore 2.5 billion people are at risk for infection in subtropical and tropical regions of the world in the absence of effective intervention.

More than 100 tropical countries have endemic dengue virus infections, and DHF has been documented in >60 of these countries. Surveillance for DF/DHF is poor in most countries, and in the past has focused primarily on DHF; the number of DF cases that occur each year can therefore only be estimated. In 1998, however, major epidemics occurred throughout Asia and the Americas, with >1.2 million cases of DF/DHF reported to the World Health Organization (WHO). Global reports of DHF have increased on average by five-fold in the past 20 years. At the beginning of the 21st century it is estimated that between 50 and 100 million cases of DF and several hundred thousand cases of DHF occur each year, depending on the epidemic activity. The case fatality rate (CFR) varies among countries, but can be as high as 10-15% in some and <1% in others.

There are four dengue virus subtypes: dengue-1 (DV-1), dengue-2 (DV-2), dengue-3 (DV-3), and dengue-4 (DV-4). Each one of these subtypes form an antigenically distinct subgroup within the flavivirus family. They are enveloped, RNA viruses that encode ten proteins: three structural proteins and seven non-structural proteins. The structural proteins are capsid (C), envelope (E) and pre-membrane precursor (preM). The intracellular life cycle of DV begins with receptor-mediated endocytosis of the virus in to cells followed by fusion of the viral envelope protein with the late endosomal membrane, which results in the release of the viral genome into the cytoplasm for replication.

Infection by DV may either be asymptomatic or characterized by fever, chills, frontal headache, myalgia, arthralgia and rash. Subsequent infection with different serotypes may result in more severe manifestations of the disease involving plasma leakage or hemorrhage (dengue hemorrhagic fever) and shock (dengue shock syndrome). Although extensive studies have been carried out over the years to understand the pathogenicity of DENV infection, little progress has been made in the development of specific anti-DV compounds. Currently there are no specific anti viral agents or vaccines against Dengue infections approved in the US.

The envelope (E) glycosylated protein, being the major structural protein present on the surface of the mature dengue virions, is a type I integral membrane protein. It has been demonstrated that the E protein of the mature Dengue forms homodimers in the anti-parallel manner (head to tail orientation). Each monomer is folded into three distinct domains, namely domain I (DI, the central N-terminal domain), domain II (DII, the dimerization domain), and domain III (PRM/E, immunoglobulin (Ig) like C terminal domain). The PRM/E domain of E protein consists of 100 amino acids (residues 303-395) of the C-terminus. This domain has been suggested to be the receptor recognition and binding domain. Ig-like fold present in the PRM/E protein is commonly associated with structures that have an adhesion function. This domain extends perpendicularly to the surface of the virus, with a tip that projects further from the virion surface than any other part of the E protein. In addition, studies have demonstrated that both recombinant PRM/E proteins and antibodies generated against PRM/E of E protein of flavivirus can inhibit entry of the flavivirus into target cells. Further, flavivirus with mutation in PRM/E of the E protein shows either attenuated virulence or the ability to escape immune neutralization.

Development of a safe and effective vaccine against dengue virus infection remains a principal public health goal. Given that the primary correlate of immunity to dengue virus is thought to be the presence of neutralizing antibodies, a prerequisite for comparing and optimizing vaccine candidates is the ability to precisely measure the neutralizing antibody responses evoked by vaccines. A combination of live attenuated virus-containing vaccines from all four serotypes has been shown to result in several complications (Guy B, Almond J W, Comp Immunol Microbiol Infect Dis. 2008 March; 31(2-3):239-52). Further, there are few reports on an adenovirus-based delivery of dengue antigens. Nevertheless, the one well recognized problem with adenovirus systems is a majority of the human population is known to have antibodies against one of the adenoviruses, and such pre-existing antibodies can cause these adeno-based vaccines to be ineffective.

Therefore, there remains a need to develop a vaccine that provides broad immunity against multiple and preferably all four serotypes of dengue virus, or universal immunity, and preferably a vaccine which is economical and effective across all serotypes. Further, there remains a need for an effective method of administering vaccines, such as DNA vaccines or DNA plasmid vaccines, to a mammal in order to provide immunization against dengue virus, either prophylactically or therapeutically.

SUMMARY OF THE INVENTION

One aspect of the present invention provides nucleic acid constructs capable of expressing a polypeptide that elicits an immune response in a mammal against more than one subtype of dengue virus. The nucleic acid constructs are comprised of an encoding nucleotide sequence and a promoter operably linked to the encoding nucleotide sequence. The encoding nucleotide sequence expresses the polypeptide, wherein the polypeptide includes domain III of envelope protein (PRM/E domain or PRM/E) from at least two different dengue virus subtypes. The promoter regulates expression of the polypeptide in the mammal.

Another aspect of the present invention provides DNA plasmid vaccines that are capable of generating in a mammal an immune response against a plurality of dengue virus subtypes. The DNA plasmid vaccines are comprised of a DNA plasmid capable of expressing a consensus dengue antigen in the mammal and a pharmaceutically acceptable excipient. The DNA plasmid is comprised of a promoter operably linked to a coding sequence that encodes the consensus dengue PRM/E antigen. The consensus dengue antigen is comprised of consensus PRM/E domains of dengue virus-subtype 1, dengue virus-subtype 2, dengue virus-subtype 3, or dengue virus-subtype 4

Another aspect of the present invention provides methods of eliciting an immune response against a plurality of subtypes of a virus in a mammal, comprising delivering a DNA plasmid vaccine to tissue of the mammal, the DNA plasmid vaccine comprising a DNA plasmid capable of expressing a plurality of consensus antigens derived from the subtypes of the virus in a cell of the mammal to elicit an immune response in the mammal, the plurality of consensus antigens comprising an antigenic domain from at least two different subtypes of the virus, and electroporating cells of the tissue with a pulse of energy at a constant current effective to permit entry of the DNA plasmids into the cells.

BRIEF DESCRIPTION OF THE DRAWINGS

FIG. 9 displays graphs showing neutralizing antibodies against each one of dengue PRM/E protein types (1 through 4) for D1-D4 prME guinea pig sera separate (administered separately)

DETAILED DESCRIPTION OF PREFERRED EMBODIMENTS

Figure 1:
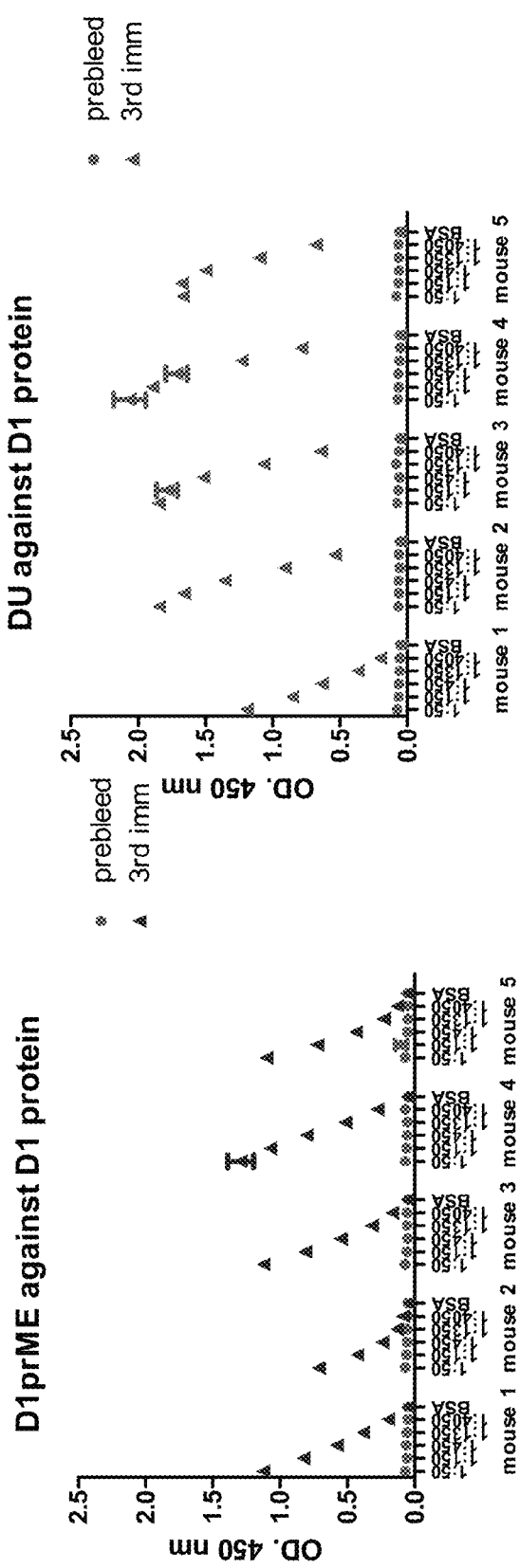
FIG. 1 displays binding titers against all dengue PRM/E domain from subtype 1 for sera from D1prME vaccinated mice versus sera from DU vaccinated mice.
Figure 2:
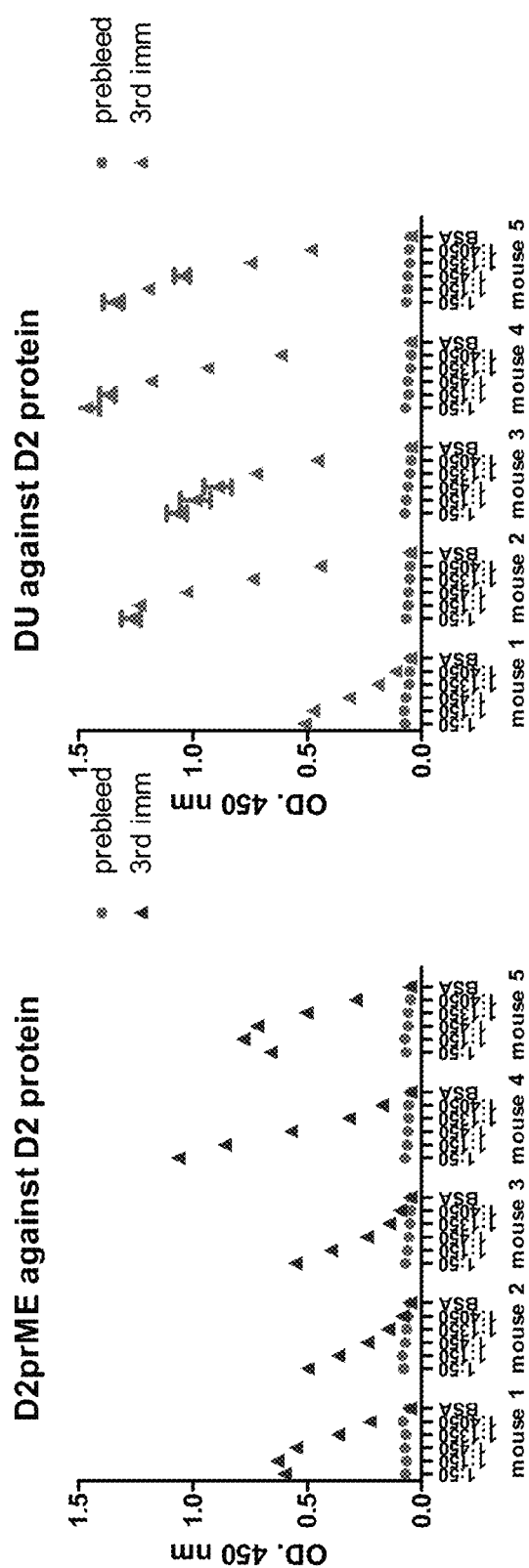
FIG. 2 displays binding titers against all dengue PRM/E domain from subtype 2 for sera from D2prME vaccinated mice versus sera from DU vaccinated mice.
Figure 3:
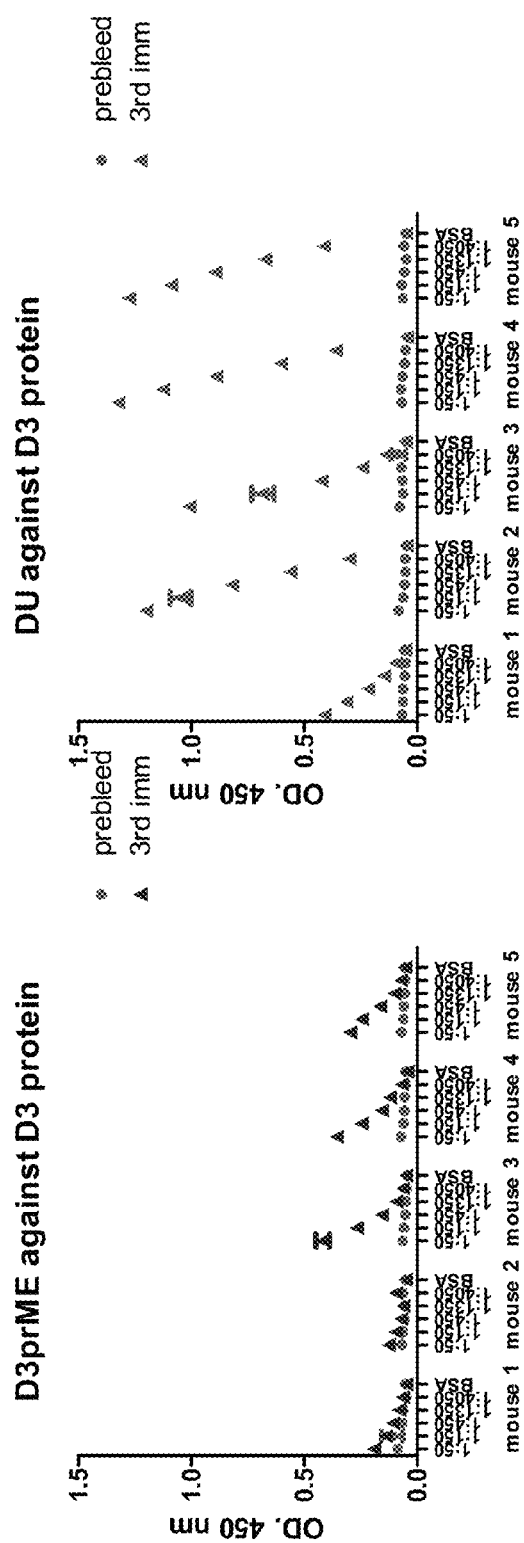
FIG. 3 displays binding titers against all dengue PRM/E domain from subtype 3 for sera from D3prME vaccinated mice versus sera from DU vaccinated mice.
Figure 4:
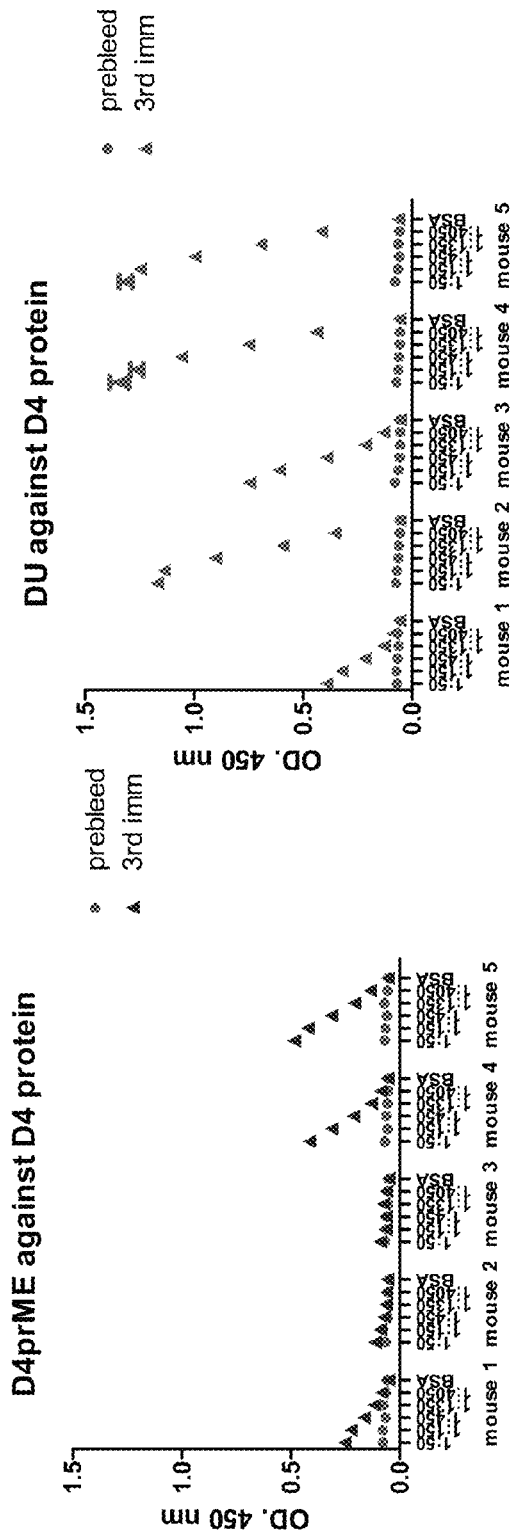
FIG. 4 displays binding titers against all dengue PRM/E domain from subtype 4 for sera from D4prME vaccinated mice versus sera from DU vaccinated mice.
Figure 5:
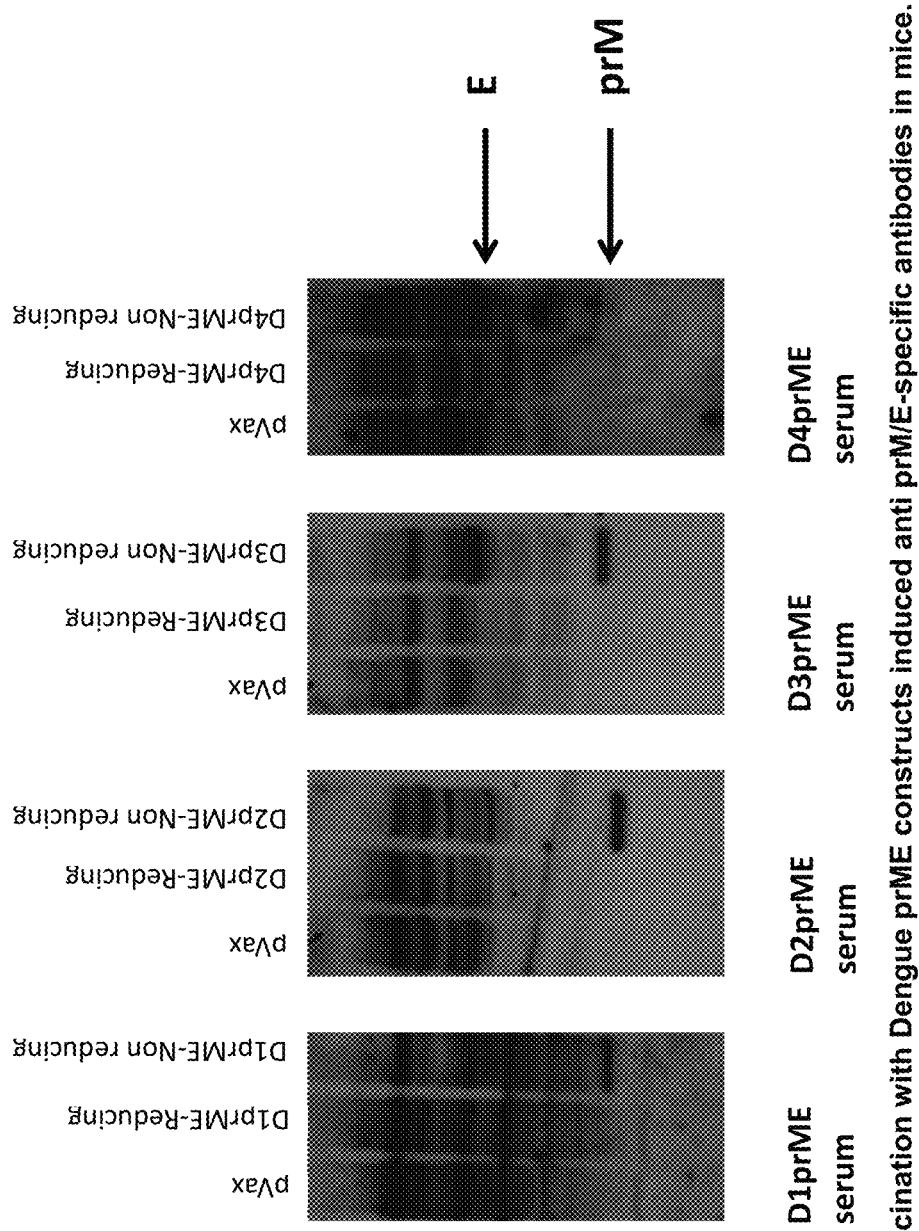
FIG. 5 displays stained gels showing binding antibodies generated against prME proteins types D1, D2, D3, and D4
Figure 6:
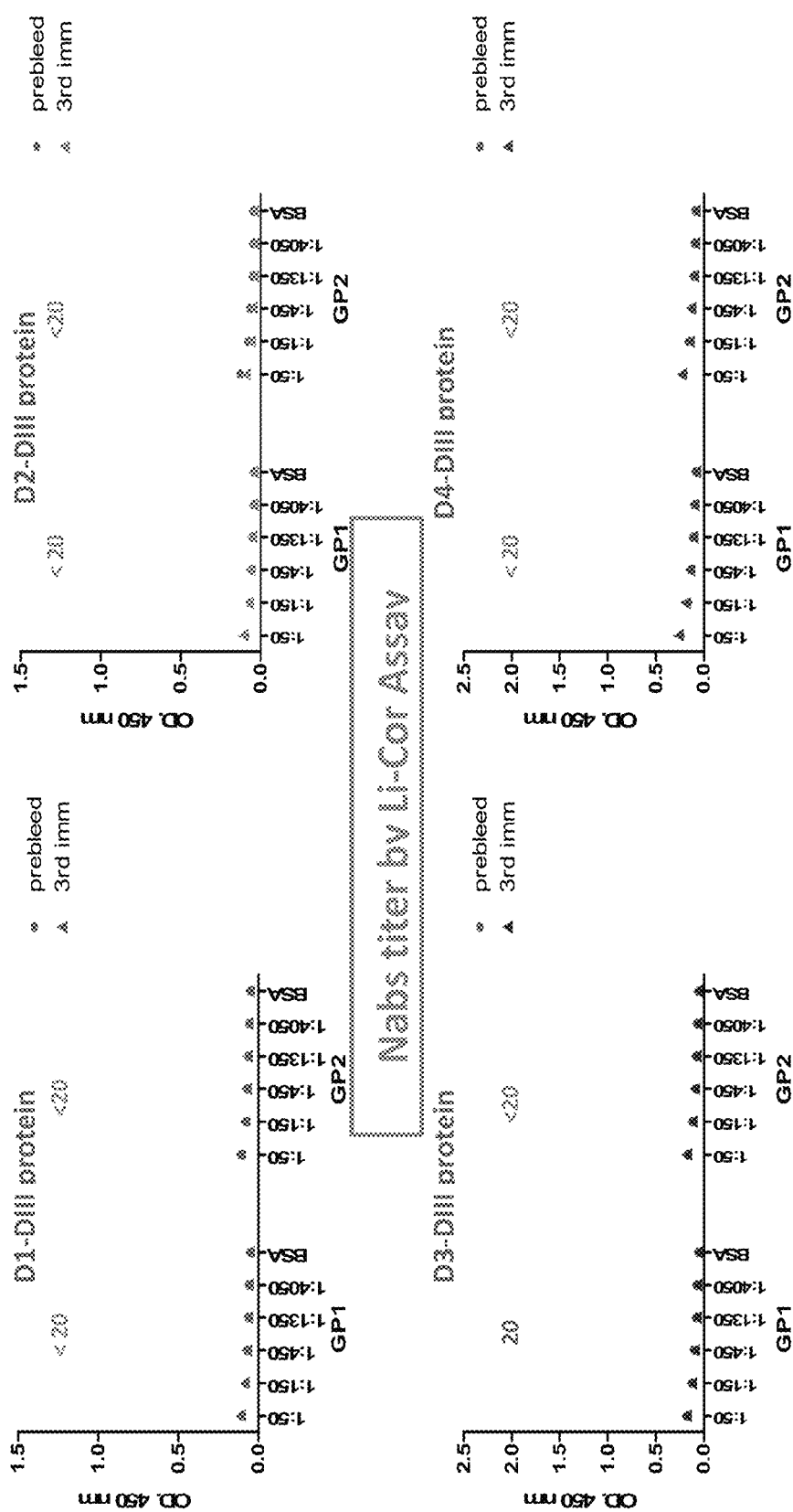
FIG. 6 displays graphs showing neutralizing antibodies against each one of dengue PRM/E protein types (1 through 4) for control guinea pig sera FIG. 7 displays graphs showing neutralizing antibodies against each one of dengue PRM/E protein types (1 through 4) for DU guinea pig sera FIG. 8 displays graphs showing neutralizing antibodies against each one of dengue PRM/E protein types (1 through 4) for D1-D4 prME guinea pig sera combined (in one mixture)
Figure 7:
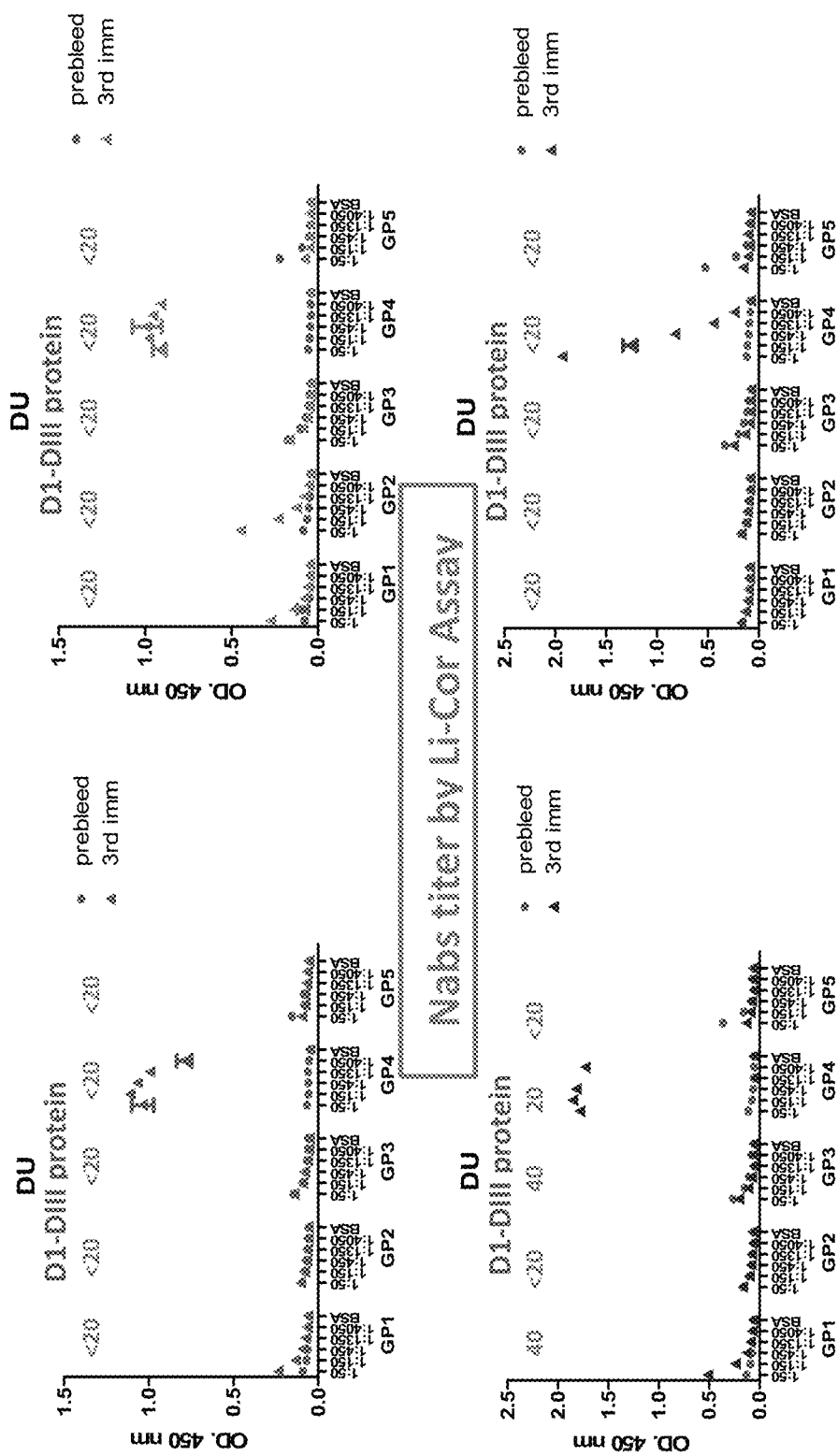
Figure 8:
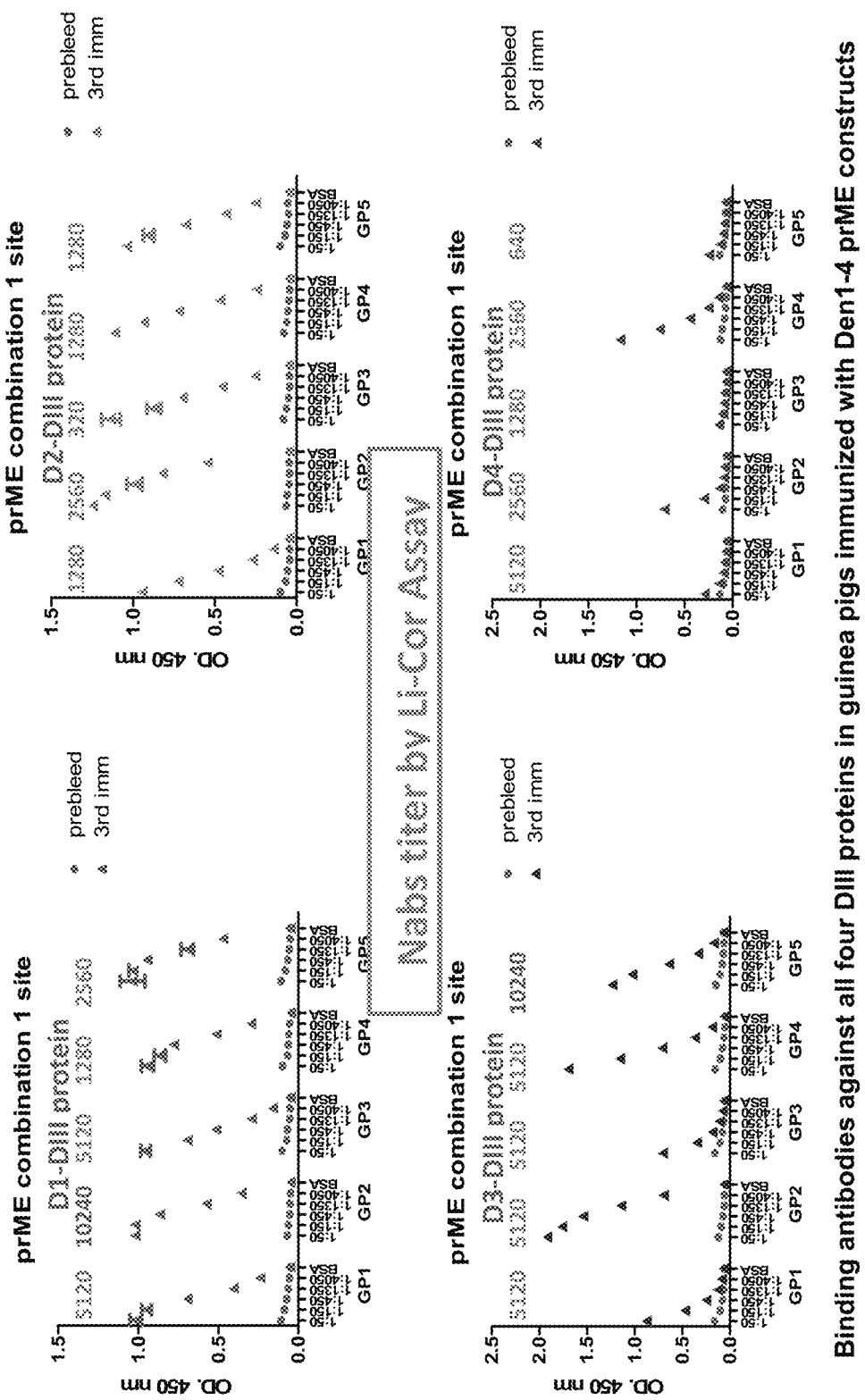
Figure 10:
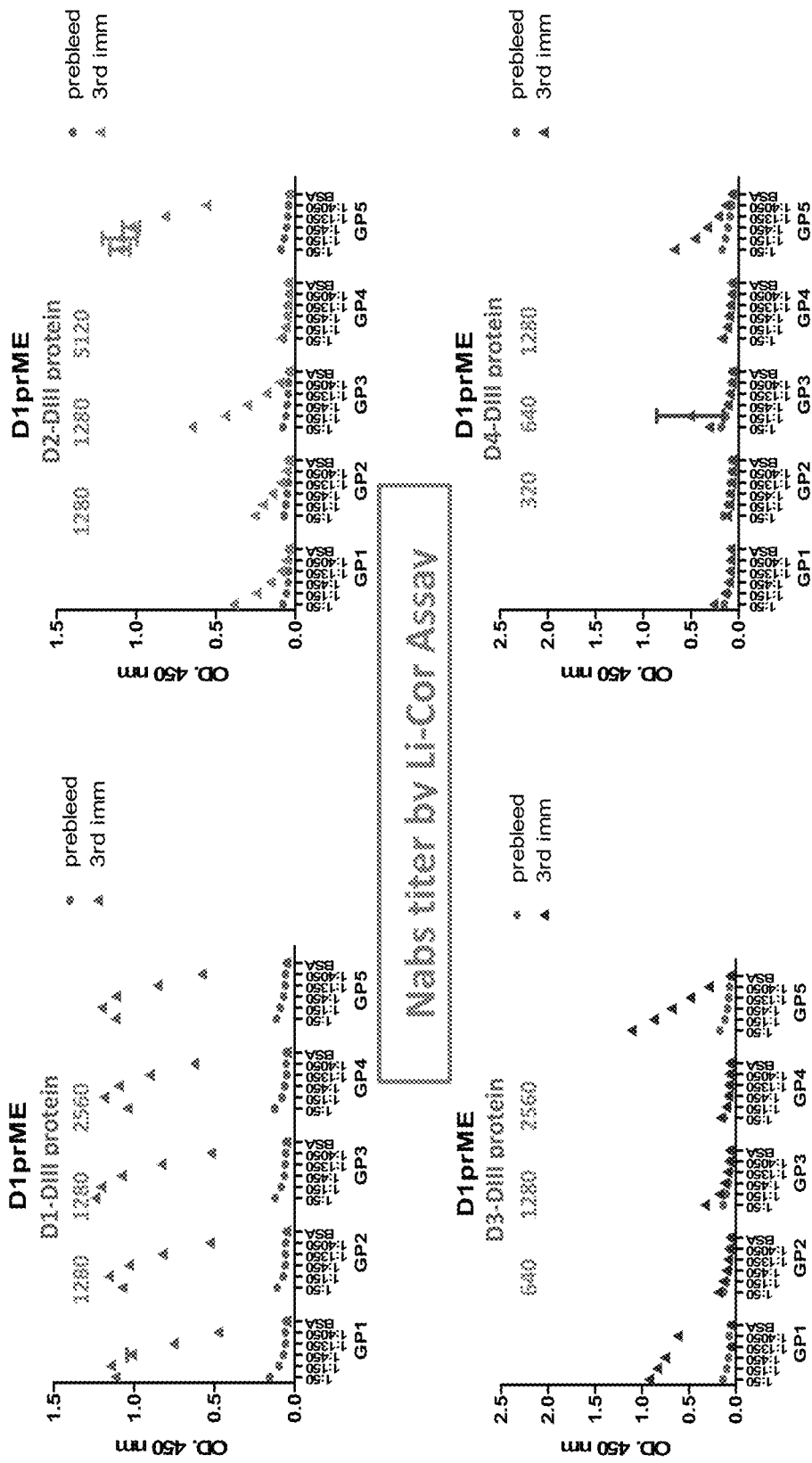
FIG. 10 displays graphs showing neutralizing antibodies against each one of dengue PRM/E protein types (1 through 4) for D1 prME guinea pig sera FIG. 11 displays graphs showing neutralizing antibodies against each one of dengue PRM/E protein types (1 through 4) for D2 prME guinea pig sera FIG. 12 displays graphs showing neutralizing antibodies against each one of dengue PRM/E protein types (1 through 4) for D3 prME guinea pig sera FIG. 13 displays graphs showing neutralizing antibodies against each one of dengue PRM/E protein types (1 through 4) for D4 prME guinea pig sera FIG. 14 displays a graph showing neutralizing antibodies against Dengue 1 virus for sera from animals vaccinated with all four D1-D4 prME FIG. 15 displays a graph showing neutralizing antibodies against Dengue 2 virus for sera from animals vaccinated with all four D1-D4 prME FIG. 16 displays a graph showing neutralizing antibodies against Dengue 3 virus for sera from animals vaccinated with all four D1-D4 prME FIG. 17 displays a graph showing neutralizing antibodies against Dengue 4 virus for sera from animals vaccinated with all four D1-D4 prME
Figure 11:
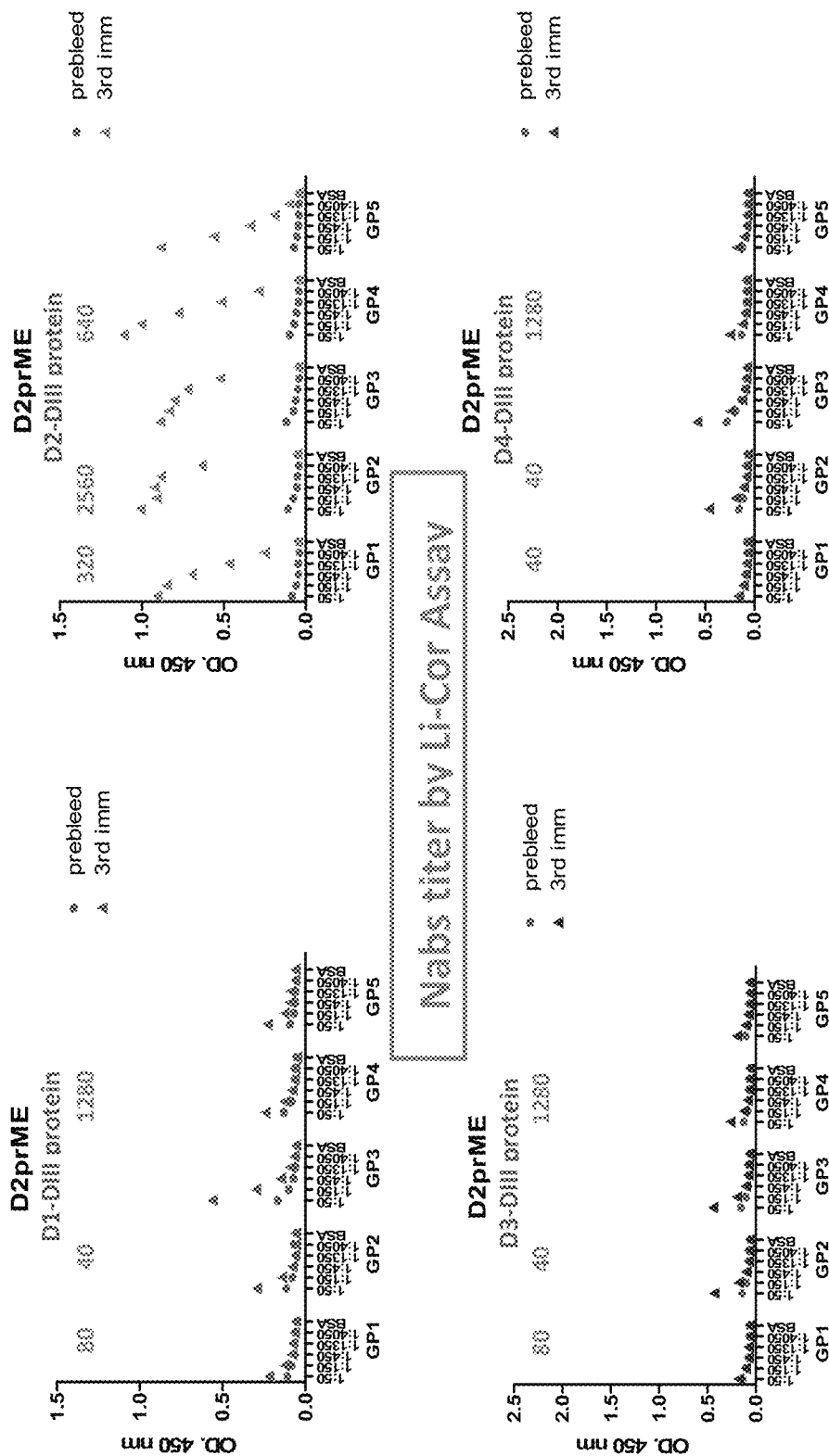
Figure 14:
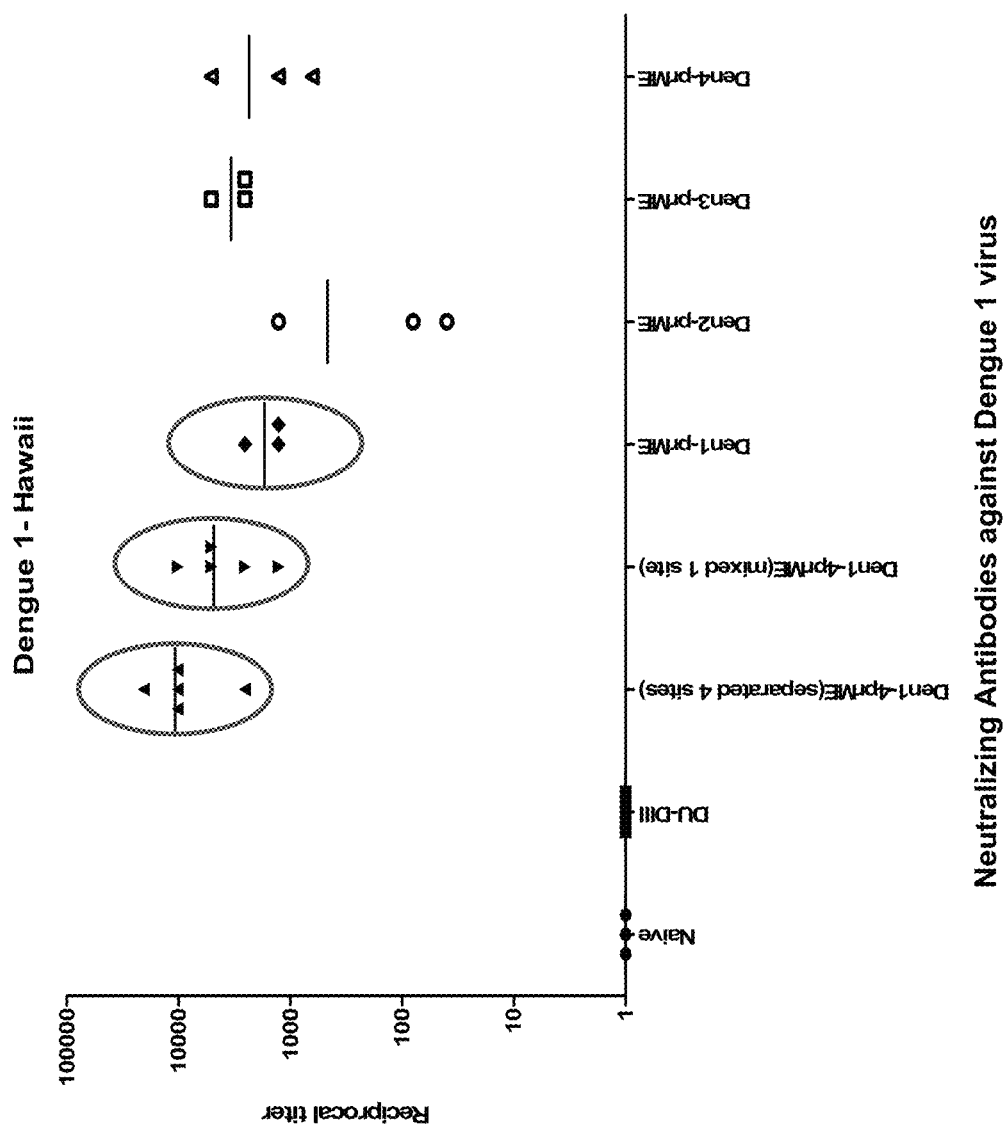

The following abbreviated, or shortened, definitions are given to help the understanding of the preferred embodiments of the present invention. The abbreviated definitions given here are by no means exhaustive nor are they contradictory to the definitions as understood in the field or dictionary meaning. The abbreviated definitions are given here to supplement or more clearly define the definitions known in the art.

Definitions

Sequence homology for nucleotides and amino acids as used herein may be determined using FASTA, BLAST and Gapped BLAST (Altschul et al., Nuc. Acids Res., 1997, 25, 3389, which is incorporated herein by reference in its entirety) and PAUP* 4.0b10 software (D. L. Swofford, Sinauer Associates, Massachusetts). Briefly, the BLAST algorithm, which stands for Basic Local Alignment Search Tool is suitable for determining sequence similarity (Altschul et al., J. Mol. Biol., 1990, 215, 403-410, which is incorporated herein by reference in its entirety). Software for performing BLAST analyses is publicly available through the National Center for Biotechnology Information. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001. "Percentage of similarity" can be calculated using PAUP* 4.0b10 software (D. L. Swofford, Sinauer Associates, Massachusetts). The average similarity of the consensus sequence is calculated compared to all sequences in the phylogenic tree.

As used herein, the term "nucleic acid construct" refers to the DNA or RNA molecules that comprise a nucleotide sequence that encodes protein. The coding sequence, or "encoding nucleic acid sequence," can include initiation and termination signals operably linked to regulatory elements including a promoter and polyadenylation signal capable of directing expression in the cells of the individual to whom the nucleic acid molecule is administered.

As used herein, the term "expressible form" refers to nucleic acid constructs that contain the necessary regulatory elements operably linked to a coding sequence that encodes a protein such that when present in the cell of the individual, the coding sequence will be expressed.

The term "constant current" is used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

The term "feedback" or "current feedback" is used interchangeably and means the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. Preferably, the feedback is accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. In some embodiments, the feedback loop is instantaneous as it is an analog closed-loop feedback.

The terms "electroporation," "electro-permeabilization," or "electro-kinetic enhancement" ("EP"), as used interchangeably herein, refer to the use of a transmembrane electric field pulse to induce microscopic pathways (pores) in a bio-membrane; their presence allows biomolecules such as plasmids, oligonucleotides, siRNA, drugs, ions, and/or water to pass from one side of the cellular membrane to the other.

The term "decentralized current" is used herein to define the pattern of electrical currents delivered from the various needle electrode arrays of the electroporation devices described herein, wherein the patterns minimize, or preferably eliminate, the occurrence of electroporation related heat stress on any area of tissue being electroporated.

The term "feedback mechanism" as used herein refers to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. The term "impedance" is used herein when discussing the feedback mechanism and can be converted to a current value according to Ohm's law, thus enabling comparisons with the preset current. In a preferred embodiment, the "feedback mechanism" is performed by an analog closed loop circuit.

The term "immune response" is used herein to mean the activation of a host's immune system, e.g., that of a mammal, in response to the introduction of a dengue antigen, e.g., universal dengue antigen, via the provided DNA plasmid vaccines. The immune response can be in the form of a cellular or humoral response, or both.

The term "consensus" or "consensus sequence" is used herein to mean a synthetic nucleic acid sequence, or corresponding polypeptide sequence, constructed based on analysis of an alignment of multiple strains of a specific dengue subtype, which yields the consensus dengue sequences of subtype-1, subtype-2, subtype-3, subtype-4, and the universal dengue described below. The consensus universal dengue can be used to induce broad immunity against multiple subtypes or serotypes of dengue virus.

The term "adjuvant" is used herein to mean any molecule added to the DNA plasmid vaccines described herein to enhance antigenicity of the dengue antigen encoded by the DNA plasmids and encoding nucleic acid sequences described hereinafter.

The term "subtype" or "serotype" is used herein interchangeably and in reference to a virus, for example dengue virus, and means genetic variants of that virus antigen such that one subtype is recognized by an immune system apart from a different subtype. For example, dengue virus subtype 1 is immunologically distinguishable from dengue virus subtype 2.

One aspect of the present invention provides nucleic acid constructs capable of expressing a polypeptide that elicits an immune response in a mammal against more than one subtype of dengue virus. The nucleic acid constructs are comprised of an encoding nucleotide sequence and a promoter operably linked to the encoding nucleotide sequence. The encoding nucleotide sequence expresses the polypeptide, wherein the polypeptide includes a PRM/E domain from at least two different dengue virus subtypes. The promoter regulates expression of the polypeptide in the mammal.

In some embodiments the nucleic acid construct can further include an IgE leader sequence operatively linked to an N-terminal end of the coding sequence and operably linked to the promoter. Preferably, the IgE leader has the sequence of SEQ ID NO: 11. The nucleic acid construct can also comprise a polyadenylation sequence attached to the C-terminal end of the coding sequence. Preferably, the nucleic acid construct is codon optimized.

In some embodiments, the encoding nucleotide sequence encodes a polypeptide that includes PRM/E domain from Dengue virus-subtype 1, Dengue virus-subtype 2, Dengue virus-subtype 3, and Dengue virus-subtype 4. In preferred embodiments, the encoding nucleotide sequence is selected from the group consisting of:

| SEQ ID NO | Description |
| --- | --- |
| 1 | Den1-prME DNA sequence |
| 2 | Den1-prME protein sequence |
| 3 | Den2-prME DNA sequence |
| 4 | Den2-prME Protein sequence |
| 5 | Den3-prME DNA sequence |
| 6 | Den3-prME protein sequence |
| 7 | Den4-prME DNA sequence |
| 8 | Den4-prME protein sequence |

Another aspect of the present invention provides DNA plasmid vaccines that are capable of generating in a mammal an immune response against a plurality of dengue virus subtypes. The DNA plasmid vaccines are comprised of a DNA plasmid capable of expressing a consensus dengue antigen in the mammal and a pharmaceutically acceptable excipient. The DNA plasmid is comprised of a promoter operably linked to a coding sequence that encodes the consensus dengue antigen. The consensus dengue antigen is comprised of consensus PRM/E domains of dengue virus-subtype 1, dengue virus-subtype 2, dengue virus-subtype 3, or dengue virus-subtype 4. Preferably, the DNA plasmid comprises a consensus dengue antigen that encodes a consensus dengue antigen selected from the group consisting of: SEQ ID NO: 2, SEQ ID NO: 4, SEQ ID NO: 6, and SEQ ID NO: 8.

In some embodiments, the DNA plasmid further comprises an IgE leader sequence attached to an N-terminal end of the coding sequence and operably linked to the promoter. Preferably, the IgE leader has the sequence Met Arg Trp Thr Trp Ile Leu Phe Leu Val Ala Ala Ala Thr Arg Val His Ser The DNA plasmid can further include a polyadenylation sequence attached to the C-terminal end of the coding sequence. Preferably, the DNA plasmid is codon optimized.

In some embodiments, the pharmaceutically acceptable excipient is an adjuvant. Preferably, the adjuvant is selected from the group consisting of: IL-12 and IL-15. In some embodiments, the pharmaceutically acceptable excipient is a transfection facilitating agent. Preferably, the transfection facilitating agent is a polyanion, polycation, or lipid, and more preferably poly-L-glutamate. Preferably, the poly-L-glutamate is at a concentration less than 6 mg/ml. Preferably, the DNA plasmid vaccine has a concentration of total DNA plasmid of 1 mg/ml or greater.

In some embodiments, the DNA plasmid comprises a plurality of unique DNA plasmids, wherein each of the plurality of unique DNA plasmids encodes a polypeptide comprising a prME dengue virus-subtype 1, dengue virus-subtype 2, dengue virus-subtype 3, or dengue virus-subtype 4.

The DNA plasmid vaccines can include a DNA plasmid comprising encoding nucleotide sequences: SEQ ID NO: 1, nucleotide sequence encoding SEQ ID NO:2, SEQ ID NO:3, nucleotide sequence encoding SEQ ID NO:4, SEQ ID NO:5, nucleotide sequence encoding SEQ ID NO:6, SEQ ID NO:7 and SEQ ID NO: 8.

In some embodiments, the DNA plasmid vaccines comprises at least two different DNA plasmids that express a dengue virus prME. In some embodiments, the DNA plasmid vaccines can include four consensus dengue virus prME (subtypes 1-4).

In some embodiments, the mammal in which the DNA plasmid vaccines generate an immune response is a primate. Preferably, the mammal is a primate. The immune response can be either a humoral response or cellular response, and preferably both.

Another aspect of the present invention provides methods of eliciting an immune response against a plurality of dengue virus subtypes in a mammal, comprising delivering a DNA plasmid vaccine to tissue of the mammal and electroporating cells of the tissue with a pulse of energy at a constant current effective to permit entry of the DNA plasmids into the cells.

In some embodiments, the methods of eliciting an immune response includes a delivering step that comprises injecting the DNA plasmid vaccine into intradermic, subcutaneous or muscle tissue.

In some embodiments, the methods of eliciting an immune response can further comprise presetting a current that is desired to be delivered to the tissue; and electroporating cells of the tissue with a pulse of energy at a constant current that equals the preset current.

In some embodiments, the methods of eliciting an immune response further comprise measuring the impedance in the electroporated cells; adjusting energy level of the pulse of energy relative to the measured impedance to maintain a constant current in the electroporated cells. The measuring and adjusting steps preferably occur within a lifetime of the pulse of energy.

In some embodiments, the electroporating step comprises delivering the pulse of energy to a plurality of electrodes according to a pulse sequence pattern that delivers the pulse of energy in a decentralized pattern.

In some embodiments of the present invention, the DNA plasmid vaccines can further include an adjuvant. In some embodiments, the adjuvant is selected from the group consisting of: alpha-interferon, gamma-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. Other genes which may be useful adjuvants include those encoding: MCP-1, MIP-1-alpha, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof. In some preferred embodiments, the adjuvant is selected from IL-12, IL-15, CTACK, TECK, or MEC.

In some embodiments, the pharmaceutically acceptable excipient is a transfection facilitating agent, which can include the following: surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents. Preferably, the transfection facilitating agent is a polyanion, polycation, including poly-L-glutamate (LGS), or lipid. Preferably, the transfection facilitating agent is poly-L-glutamate, and more preferably, the poly-L-glutamate is present in the DNA plasmid vaccine at a concentration less than 6 mg/ml.

In some embodiments, the concentration of poly-L-glutamate in the DNA plasmid vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

In some embodiments, the DNA plasmid vaccine can be delivered to a mammal to elicit an immune response; preferably the mammal is a primate, including human and nonhuman primate, a cow, pig, chicken, dog, or ferret. More preferably, the mammal is a human primate.

One aspect of the present invention relates to methods of eliciting an immune response against a plurality of subtypes of a virus in a mammal. The methods include delivering a DNA plasmid vaccine to tissue of the mammal, and electroporating cells of the tissue with a pulse of energy at a constant current effective to permit entry of the DNA plasmids into the cells. The DNA plasmid vaccine comprises a DNA plasmid capable of expressing a plurality of consensus antigens derived from the subtypes of the virus in a cell of the mammal to elicit an immune response in the mammal, the plurality of consensus antigens comprising an antigenic domain from at least two different subtypes of the virus.

One aspect of the present invention relates to methods of eliciting an immune response against a plurality of dengue virus subtypes in a mammal. The methods include delivering a DNA plasmid vaccine to tissue of the mammal, the DNA plasmid vaccine comprising a DNA plasmid capable of expressing a consensus dengue antigen in a cell of the mammal to elicit an immune response in the mammal, the consensus dengue antigen comprising consensus sequences coding for prME protein from at least two dengue subtypes, and preferably all four dengue subtypes. The dengue subtypes include subtype-1, subtype-2, subtype-3, and subtype-4. The methods of eliciting an immune response including electroporating cells of the tissue with a pulse of energy at a constant current effective to permit entry of the DNA plasmids in the cells.

In some embodiments, the methods of the present invention include the delivering step, which comprises injecting the DNA plasmid vaccine into intradermic, subcutaneous or muscle tissue. Preferably, these methods include using an in vivo electroporation device to preset a current that is desired to be delivered to the tissue; and electroporating cells of the tissue with a pulse of energy at a constant current that equals the preset current. In some embodiments, the electroporating step further comprises: measuring the impedance in the electroporated cells; adjusting energy level of the pulse of energy relative to the measured impedance to maintain a constant current in the electroporated cells; wherein the measuring and adjusting steps occur within a lifetime of the pulse of energy.

In some embodiments, the electroporating step comprises delivering the pulse of energy to a plurality of electrodes according to a pulse sequence pattern that delivers the pulse of energy in a decentralized pattern.

The present invention also comprises DNA fragments that encode a polypeptide capable of eliciting an immune response in a mammal substantially similar to that of the non-fragment for at least one dengue virus subtype. The DNA fragments are fragments selected from at least one of the various encoding nucleotide sequences of the present invention, including SEQ ID NO: 1, nucleotide sequence encoding SEQ ID NO:2, SEQ ID NO:3, nucleotide sequence encoding SEQ ID NO:4, SEQ ID NO:5, nucleotide sequence encoding SEQ ID NO:6, SEQ ID NO:7 and SEQ ID NO: 8, and can be any of the following described DNA fragments, as it applies to the specific encoding nucleic acid sequence provided herein. In some embodiments, DNA fragments can comprise 30 or more, 45 or more, 60 or more, 75 or more, 90 or more, 120 or more, 150 or more, 180 or more, 210 or more, 240 or more, 270 or more, 300 or more, 320 or more, 340 or more, or 360 or more nucleotides. In some embodiments, DNA fragments can comprise coding sequences for the immunoglobulin E (IgE) leader sequences. In some embodiments, DNA fragments can comprise fewer than 60, fewer than 75, fewer than 90, fewer than 120, fewer than 150, fewer than 180, fewer than 210, fewer than 240, fewer than 270, fewer than 300, fewer than 320, fewer than 340, or fewer than 360 nucleotides.

The present invention includes polypeptides encoded by the encoding nucleotide sequences and can include polypeptides having amino acid sequences of SEQ ID NOS: 2, 4, 6, and 8. The present invention also comprises polypeptide fragments that are capable of eliciting an immune response in a mammal substantially similar to that of the non-fragment for at least one dengue subtype. The polypeptide fragments are selected from at least one of the various polypeptide sequences of the present invention, including SEQ ID NOS: 2, 4, 6, and 8, and can be any of the following described polypeptide fragments, as it applies to the specific polypeptide sequence provided herein. In some embodiments, polypeptide fragments can comprise 15 or more, 30 or more, 45 or more, 60 or more, 75 or more, 90 or more, 100 or more, 110 or more, or 120 or more amino acids. In some embodiments, polypeptide fragments can comprise fewer than 30, fewer than 45, fewer than 60, fewer than 75, fewer than 90, fewer than 100, fewer than 110, or fewer than 120 amino acids.

The determination of a functional fragment eliciting an immune response in a mammal substantially similar to that of the non-fragment for at least one dengue subtype can be readily determined by one of ordinary skill. The fragment can be analyzed to contain at least one, preferably more, antigenic epitopes as provided by a publicly available database, such as National Center for Biotechnology Information (NCBI). In addition, immune response studies can be routinely assessed using mice and antibody titers and ELISpots analysis, such as that shown in the Examples below.

Vaccines

In some embodiments, the invention provides improved vaccines by providing proteins and genetic constructs that encode proteins with epitopes that make them particularly effective as immunogens against which immune responses can be induced. Accordingly, vaccines can be provided to induce a therapeutic or prophylactic immune response.

According to some embodiments of the invention, a vaccine according to the invention is delivered to an individual to modulate the activity of the individual's immune system and thereby enhance the immune response. When a nucleic acid molecule that encodes the protein is taken up by cells of the individual the nucleotide sequence is expressed in the cells and the protein is thereby delivered to the individual. Aspects of the invention provide methods of delivering the coding sequences of the protein on nucleic acid molecule such as plasmid.

According to some aspects of the present invention, compositions and methods are provided which prophylactically and/or therapeutically immunize an individual.

When taken up by a cell, the DNA plasmids can remain in the cell as separate genetic material. Alternatively, RNA may be administered to the cell. It is also contemplated to provide the genetic construct as a linear minichromosome including a centromere, telomeres and an origin of replication. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the mammals to whom the nucleic acid construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from simian virus 40 (SV40), mouse mammary tumor virus (MMTV) promoter, human immunodeficiency virus (HIV) such as the bovine immunodeficiency virus (BIV) long terminal repeat (LTR) promoter, Moloney virus, avian leukosis virus (ALV), cytomegalovirus (CMV) such as the CMV immediate early promoter, Epstein Barr virus (EBV), Rous sarcoma virus (RSV) as well as promoters from human genes such as human actin, human myosin, human hemoglobin, human muscle creatine and human metalthionein; in other embodiments, promoters can be tissue specific promoters, such as muscle or skin specific promoters, natural or synthetic. Examples of such promoters are described in US patent application publication no. US20040175727, which is incorporated hereby in its entirety.

Examples of polyadenylation signals useful to practice the present invention, especially in the production of a genetic vaccine for humans, include but are not limited to SV40 polyadenylation signals, LTR polyadenylation signals, bovine growth hormone (bGH) polyadenylation signals, human growth hormone (hGH) polyadenylation signals, and human β-globin polyadenylation signals. In particular, the SV40 polyadenylation signal that is in pCEP4 plasmid (Invitrogen, San Diego, Calif.), referred to as the SV40 polyadenylation signal, can be used.

In addition to the regulatory elements required for DNA expression, other elements may also be included in the DNA molecule. Such additional elements include enhancers. The enhancer may be selected from the group including but not limited to: human actin, human myosin, human hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In order to maximize protein production, regulatory sequences may be selected which are well suited for gene expression in the cells the construct is administered into. Moreover, codons that encode said protein may be selected which are most efficiently transcribed in the host cell. One having ordinary skill in the art can produce DNA constructs that are functional in the cells.

In some embodiments, nucleic acid constructs may be provided in which the coding sequences for the proteins described herein are linked to IgE signal peptide. In some embodiments, proteins described herein are linked to IgE signal peptide.

In some embodiments for which protein is used, for example, one having ordinary skill in the art can, using well known techniques, produce and isolate proteins of the invention using well known techniques. In some embodiments for which protein is used, for example, one having ordinary skill in the art can, using well known techniques, inserts DNA molecules that encode a protein of the invention into a commercially available expression vector for use in well known expression systems. For example, the commercially available plasmid pSE420 (Invitrogen, San Diego, Calif.) may be used for production of protein in Escherichia coli (E. coli). The commercially available plasmid pYES2 (Invitrogen, San Diego, Calif.) may, for example, be used for production in Saccharomyces cerevisiae strains of yeast. The commercially available MAXBAC™ complete baculovirus expression system (Invitrogen, San Diego, Calif.) may, for example, be used for production in insect cells. The commercially available plasmid pcDNA or pcDNA3 (Invitrogen, San Diego, Calif.) may, for example, be used for production in mammalian cells such as Chinese hamster ovary (CHO) cells. One having ordinary skill in the art can use these commercial expression vectors and systems or others to produce protein by routine techniques and readily available starting materials. (See e.g., Sambrook et al., Molecular Cloning a Laboratory Manual, Second Ed. Cold Spring Harbor Press (1989)). Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers are readily available and known in the art for a variety of hosts. See e.g., Sambrook et al., Molecular Cloning a Laboratory Manual, Second Ed. Cold Spring Harbor Press (1989). Genetic constructs include the protein coding sequence operably linked to a promoter that is functional in the cell line, or cells of targeted tissue, into which the constructs are transfected. Examples of constitutive promoters include promoters from cytomegalovirus (CMV) or SV40. Examples of inducible promoters include mouse mammary leukemia virus or metallothionein promoters. Those having ordinary skill in the art can readily produce genetic constructs useful for transfecting cells with DNA that encodes protein of the invention from readily available starting materials. The expression vector including the DNA that encodes the protein is used to transform the compatible host which is then cultured and maintained under conditions wherein expression of the foreign DNA takes place.

The protein produced is recovered from the culture, either by lysing the cells or from the culture medium as appropriate and known to those in the art. One having ordinary skill in the art can, using well known techniques, isolate protein that is produced using such expression systems. The methods of purifying protein from natural sources using antibodies which specifically bind to a specific protein as described above may be equally applied to purifying protein produced by recombinant DNA methodology.

In addition to producing proteins by recombinant techniques, automated peptide synthesizers may also be employed to produce isolated, essentially pure protein. Such techniques are well known to those having ordinary skill in the art and are useful if derivatives which have substitutions not provided for in DNA-encoded protein production.

The nucleic acid molecules may be delivered using any of several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. Preferably, the nucleic acid molecules such as the DNA plasmids described herein are delivered via DNA injection and along with in vivo electroporation.

Routes of administration include, but are not limited to, intramuscular, intranasally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, traditional syringes, needleless injection devices, "microprojectile bombardment gone guns", or other physical methods such as electroporation ("EP"), "hydrodynamic method", or ultrasound.

Examples of electroporation devices and electroporation methods preferred for facilitating delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 are adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

The following is an example of methods of the present invention, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The present invention is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 μs, 20 μs, 10 μs or 1 μs, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

A pharmaceutically acceptable excipient can include such functional molecules as vehicles, adjuvants, carriers or diluents, which are known and readily available to the public. Preferably, the pharmaceutically acceptable excipient is an adjuvant or transfection facilitating agent. In some embodiments, the nucleic acid molecule, or DNA plasmid, is delivered to the cells in conjunction with administration of a polynucleotide function enhancer or a genetic vaccine facilitator agent (or transfection facilitating agent). Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in U.S. Ser. No. 021,579 filed Apr. 1, 1994, which is incorporated herein by reference. The transfection facilitating agent can be administered in conjunction with nucleic acid molecules as a mixture with the nucleic acid molecule or administered separately simultaneously, before or after administration of nucleic acid molecules. Examples of transfection facilitating agents includes surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

In some preferred embodiments, the DNA plasmids are delivered with an adjuvant that are genes for proteins which further enhance the immune response against such target proteins. Examples of such genes are those which encode other cytokines and lymphokines such as alpha-interferon, gamma-interferon, platelet derived growth factor (PDGF), TNFα, TNFβ, GM-CSF, epidermal growth factor (EGF), IL-1, IL-2, IL-4, IL-5, IL-6, IL-10, IL-12, IL-18, MHC, CD80, CD86 and IL-15 including IL-15 having the signal sequence deleted and optionally including the signal peptide from IgE. Other genes which may be useful include those encoding: MCP-1, MIP-1α, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The DNA plasmid vaccines according to the present invention comprise DNA quantities of from about 1 nanogram to 10 milligrams; about 1 microgram to about 10 milligrams; or preferably about 0.1 microgram to about 10 milligrams; or more preferably about 100 microgram to about 1 milligram. In some preferred embodiments, DNA plasmid vaccines according to the present invention comprise about 5 nanogram to about 1000 micrograms of DNA. In some preferred embodiments, the DNA plasmid vaccines contain about 10 nanograms to about 800 micrograms of DNA. In some preferred embodiments, the DNA plasmid vaccines contain about 0.1 to about 500 micrograms of DNA. In some preferred embodiments, the DNA plasmid vaccines contain about 1 to about 350 micrograms of DNA. In some preferred embodiments, the DNA plasmid vaccines contain about 25 to about 250 micrograms of DNA. In some preferred embodiments, the DNA plasmid vaccines contain about 100 microgram to about 1 milligram DNA.

The DNA plasmid vaccines according to the present invention are formulated according to the mode of administration to be used. In cases where DNA plasmid vaccines are injectable compositions, they are sterile, and/or pyrogen free and/or particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. In some embodiments, a stabilizing agent that allows the formulation to be stable at room or ambient temperature for extended periods of time, such as LGS or other polycations or polyanions is added to the formulation.

In some embodiments, methods of eliciting an immune response in mammals against a consensus dengue antigen include methods of inducing mucosal immune responses. Such methods include administering to the mammal one or more of CTACK protein, TECK protein, MEC protein and functional fragments thereof or expressible coding sequences thereof in combination with an DNA plasmid including a consensus dengue antigen, described above. The one or more of CTACK protein, TECK protein, MEC protein and functional fragments thereof may be administered prior to, simultaneously with or after administration of the DNA plasmid dengue vaccines provided herein. In some embodiments, an isolated nucleic acid molecule that encodes one or more proteins of selected from the group consisting of: CTACK, TECK, MEC and functional fragments thereof is administered to the mammal.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Preferably the DNA formulations for use with a muscle or skin EP device described herein have high DNA concentrations, preferably concentrations that include microgram to tens of milligram quantities, and preferably milligram quantities, of DNA in small volumes that are optimal for delivery to the skin, preferably small injection volume, ideally 25-200 microliters (μL). In some embodiments, the DNA formulations have high DNA concentrations, such as 1 mg/mL or greater (mg DNA/volume of formulation). More preferably, the DNA formulation has a DNA concentration that provides for gram quantities of DNA in 200 μL of formula, and more preferably gram quantities of DNA in 100 μL of formula.

The DNA plasmids for use with the EP devices of the present invention can be formulated or manufactured using a combination of known devices and techniques, but preferably they are manufactured using an optimized plasmid manufacturing technique that is described in U.S. application Ser. No. 12/126,611 which published as US Publication No. 20090004716, which published Jan. 1, 2009. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in US Publication No. 20090004716 and those described in U.S. Pat. No. 7,238,522, which issued on Jul. 3, 2007. The high concentrations of plasmids used with the skin EP devices and delivery techniques described herein allow for administration of plasmids into the ID/SC space in a reasonably low volume and aids in enhancing expression and immunization effects. The publications, US Publication No. 20090004716 and U.S. Pat. No. 7,238,522, are hereby incorporated in their entirety.

Dengue prM/E—Rationale

- prM prevents premature fusion of the E protein during virus maturation by forming a non-infectious immature virus particles, prM-E heterodimeric complex
- The immature particles transit through a low pH environment of the Golgi compartment, at this stage, a reversible conformational change occurs in E protein prior to processing of prM.
- After cleavage of prM to M by cellular serine protease in the trans-Golgi network results in an irreversible conformational change in E which maintains the integrity of the neutralizing epitopes.

Experimental Design

| GROUP | NO. OF ANIMALS | PLASMID | NO. OF INJECTION SITES | PLASMID DOSE PER INJECTION |
|---|---|---|---|---|
| 1 | 5 | | 1 | 100 ug |
| 2 | 5 | | 1 | 100 ug |
| 3 | 5 | | 1 | 100 ug |
| 4 | 5 | | 1 | 100 ug |
| 5 | 5 | | 1 | 100 ug |
| 6 | 5 | | 4 | 100 ug each; 400 ug in total |
| 7 | 5 | | 1 | 100 ug each; 400 ug in total |
| 8 | 3 | | NONE | NONE |

Animal Received 3 Immunizations with 3P Cellectra (ID), 3 Weeks Apart and Bleed Every 3 Weeks Dengue Li-Cor Assay

- 2-fold serial dilutions of serum in 96-well plate: 50 μl/well
- Add 50 pfu virus to each well: 50 ul/well Incubate @ 37° C. for 1 hour to allow for neutralization
- Add entire mixture (100 uL) to VERO cells (seed $1.5\times10^4$/well) Incubate plates 4 days @ 37° C.
- Fix cells using 3.7% formaldehyde for 30 minutes
- Wash and permeabilize using 0.1% TritonX-100/PBS
- Perform cell-based ELISA:
- Mouse 4G2 mAb
- Biotinylated anti-mouse IgG
- IRDye 800CW Streptavidin+5 mM DRAQ5 cocktail solution
- Wash, dry and scan plates using Li-Cor Aerius system
- Calculate 800 nm/700 nm ratios
- . . . Dengue $PRNT_{50}$ Assay Day 1

- Plate VERO cells—6 well format
- ($7.5\times10^5$-$1.0\times10^6$ cells/well)

Day 2

- Incubate 50 pfu virus/well+serum (1 hour @ 37° C.)
- Add mixture to monolayer (1 hour @ 37° C.)
- Overlay with 1% methyl-cellulose in 2% medium 199
- Incubate for 5 days post-infection (37° C.)

Day 7

- Fix and stain with 0.05% Crystal violet/20% methanol mixture
- (RT for 2 hours)
- Wash plates with $dH_2O$, dry and count plaques
- Calculate 50% reduction relative to virus only control
- Neutralization titers are defined as the reciprocal of the highest serum dilution that
- reduces plaque count by >50% compared to controls without sera Focus Diagnostics FRNT Assay
- 24-well plates
- 4-fold dilution of serum
- 4 day incubation period
- Immunofocus development of plaques Ph1 Clinical Study Virus Neutralizing Antibody Responses Determined by LiCor, FRNT and PRNT Assays

| Protocol | Treatment Group | Time Point | Blinding ID | Merck Li-Cor DEN1 Titers | HBI PRNT DEN1 Titers | Focus FRNT DEN1 Titers |
|---|---|---|---|---|---|---|
| HBV-001 | 10 μg DEN1-80E | week 10 | 69 | 320 | 44 | 152 |
| HBV-001 | 1.25 mg Alhyd. | week 10 | 42 | 80 | 30 | 32 |
| HBV-001 | | week 10 | 84 | 5 | 5 | 5 |
| HBV-001 | | week 10 | 7 | 320 | 91 | 137 |
| HBV-001 | | week 10 | 18 | 40 | 32 | 28 |
| HBV-001 | | week 10 | 49 | 5 | 5 | 5 |
| | | | GMT | 45 | 21 | 28 |
| HBV-001 | 50 μg DEN1-80E | week 10 | 77 | 640 | 502 | 370 |
| HBV-001 | 1.25 mg Alhyd. | week 10 | 28 | 160 | 58 | 25 |
| HBV-001 | | week 10 | 95 | 80 | 5 | 5 |
| HBV-001 | | week 10 | 66 | 80 | 37 | 20 |
| HBV-001 | | week 10 | 53 | 320 | 62 | 62 |
| HBV-001 | | week 10 | 47 | 80 | 14 | 29 |
| | | | GMT | 160 | 41 | 34 |
| HBV-001 | Placebo | week 10 | 25 | 5 | 5 | 5 |
| HBV-001 | | week 10 | 86 | 5 | 5 | 5 |
| HBV-001 | | week 10 | 20 | 5 | 5 | 5 |
| HBV-001 | | week 10 | 12 | 5 | 5 | 5 |
| | | | GMT | 5 | 5 | 5 |

What is claimed:

1. A nucleic acid construct for expressing a polypeptide that elicits an immune response in a mammal against more than one subtype of Dengue virus, comprising:

an encoding nucleotide sequence that expresses the polypeptide, wherein the polypeptide includes consensus prME proteins from at least two different Dengue virus subtypes, and a promoter that regulates expression of the polypeptide in the mammal and is operably linked to the encoding nucleotide sequence, wherein the encoding nucleotide sequence comprises at least two nucleic acid sequences selected from the group consisting of a nucleotide sequence encoding SEQ ID NO: 2, a nucleotide sequence encoding SEQ ID NO: 4, a nucleotide sequence encoding SEQ ID NO: 6, and a nucleotide sequence encoding SEQ ID NO: 8.

2. The nucleic acid construct of claim 1, further comprising an IgE leader sequence operatively linked to the 5'-end of the coding sequence and operably linked to the promoter.

3. The nucleic acid construct of claim 1, further comprising a polyadenylation sequence attached to the 3'-end of the coding sequence.

4. The nucleic acid construct of claim 1, wherein the nucleic acid construct is codon optimized.

5. The nucleic acid construct of claim 1, wherein the encoding nucleotide sequence encodes a polypeptide that includes at least two prME proteins selected from the group consisting of dengue virus-subtype 1, dengue virus-subtype 2, dengue virus-subtype 3, and dengue virus-subtype 4.

6. The nucleic acid construct of claim 1, wherein the encoding nucleotide sequence comprises at least two nucleic acid sequences selected from the group consisting of SEQ ID NO: 1, SEQ ID NO: 3, SEQ ID NO: 5, and SEQ ID NO: 7.

7. A DNA plasmid vaccine for generating in a mammal an immune response against a plurality of dengue virus subtypes, comprising:
    at least one DNA plasmid for expressing at least one consensus dengue antigen in a cell of the mammal in a quantity effective to elicit an immune response in the mammal, wherein at least one consensus dengue antigen is selected from the group consisting of SEQ ID NO: 2, SEQ ID NO: 4, SEQ ID NO: 6, and SEQ ID NO: 8 and a combination thereof, and
    a pharmaceutically acceptable excipient;
    the DNA plasmid comprising a promoter operably linked to a coding sequence that encodes the consensus dengue antigen.

8. The DNA plasmid vaccine of claim 7, wherein the DNA plasmid further comprises an IgE leader sequence attached to the 5'-end of the coding sequence and operably linked to the promoter.

9. The DNA plasmid vaccine of claim 7, wherein the DNA plasmid further comprises a polyadenylation sequence attached to the 3'-end of the coding sequence.

10. The DNA plasmid vaccine of claim 7, wherein the DNA plasmid is codon optimized.

11. The DNA plasmid vaccine of claim 7, wherein the pharmaceutically acceptable excipient is an adjuvant.

12. The DNA plasmid vaccine of claim 11, wherein the adjuvant is selected from the group consisting of: IL-12 and IL-15.

13. The DNA plasmid vaccine of claim 7, wherein the pharmaceutically acceptable excipient is a transfection facilitating agent.

14. The DNA plasmid vaccine of claim 13, wherein the transfection facilitating agent is a polyanion, polycation, or lipid.

15. The DNA plasmid vaccine of claim 13, wherein the transfection facilitating agent is poly-L-glutamate at a concentration less than 6 mg/ml.

16. The DNA plasmid vaccine of claim 7, wherein the DNA plasmid vaccine has a concentration of total DNA plasmid of 1 mg/ml or greater.

17. The DNA plasmid vaccine of claim 7, wherein the vaccine comprises a plurality of unique DNA plasmids, wherein each of the plurality of unique DNA plasmids encodes a polypeptide comprising at least one consensus prME protein selected from the group consisting of SEQ ID NO: 2, SEQ ID NO: 4, SEQ ID NO: 6, and SEQ ID NO: 8.

18. The DNA plasmid vaccine of claim 7, wherein the encoding nucleotide sequence comprises one or more sequences selected from the group consisting of SEQ ID NO: 1, SEQ ID NO: 3, SEQ ID NO: 5, and SEQ ID NO: 7.

19. The DNA plasmid vaccine of claim 7, comprising at least two different DNA plasmids that express a Dengue virus prME protein, the plasmids selected from the group consisting of:
    a DNA plasmid comprising a sequence that encodes SEQ ID NO:2,
    a DNA plasmid comprising a sequence that encodes SEQ ID NO:4,
    a DNA plasmid comprising a sequence that encodes SEQ ID NO:6, and
    a DNA plasmid comprising a sequence that encodes SEQ ID NO:8.

20. The DNA plasmid vaccine of claim 7, comprising:
    the DNA plasmid comprising a sequence that encodes SEQ ID NO:2,
    the DNA plasmid comprising a sequence that encodes SEQ ID NO:4,
    the DNA plasmid comprising a sequence that encodes SEQ ID NO:6, and
    the DNA plasmid comprising a sequence that encodes SEQ ID NO:8.

21. The DNA plasmid vaccine of claim 7, wherein the nucleotide sequence encoding SEQ ID NO:2 is SEQ ID NO: 1, wherein the nucleotide sequence encoding SEQ ID NO:4 is SEQ ID NO: 3, wherein the nucleotide sequence encoding SEQ ID NO:6 is SEQ ID NO: 5, and wherein the nucleotide sequence encoding SEQ ID NO:8 is SEQ ID NO: 7.

22. The DNA plasmid vaccine of claim 7, wherein the mammal is a nonhuman primate.

23. The DNA plasmid vaccine of claim 7, wherein the immune response is selected from the group consisting of a humoral response, a cellular response, and a combination thereof.

24. A method of eliciting an immune response against a plurality of subtypes of a dengue virus in a mammal, comprising,
    delivering the DNA plasmid vaccine of claim 7 to tissue of the mammal, and
    electroporating cells of the tissue with a pulse of energy at a constant current effective to permit entry of DNA plasmids in said DNA plasmid vaccine into the cells.

25. The method of claim 24, wherein the delivering step comprises:
    injecting the DNA plasmid vaccine into intradermic, subcutaneous or muscle tissue.

26. The method of claim 24, further comprising:
    presetting a current that is desired to be delivered to the tissue; and
    electroporating cells of the tissue with a pulse of energy at a constant current that equals the preset current.

27. The method of claim 24, wherein the electroporating step further comprises:
    measuring the impedance in the electroporated cells;
    adjusting energy level of the pulse of energy relative to the measured impedance to maintain a constant current in the electroporated cells;
    wherein the measuring and adjusting steps occur within a lifetime of the pulse of energy.

28. The method of claim 24, wherein the electroporating step comprises:
    delivering the pulse of energy to a plurality of electrodes according to a pulse sequence pattern that delivers the pulse of energy in a decentralized pattern.

* * * * *